United States Patent
Cost et al.

(10) Patent No.: US 10,435,677 B2
(45) Date of Patent: Oct. 8, 2019

(54) GENETICALLY MODIFIED HUMAN CELL WITH A CORRECTED MUTANT SICKLE CELL MUTATION

(71) Applicant: Sangamo Therapeutics, Inc., Richmond, CA (US)

(72) Inventors: Gregory J. Cost, Richmond, CA (US); Jeffrey C. Miller, Richmond, CA (US); Lei Zhang, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

(21) Appl. No.: 15/511,858

(22) PCT Filed: Sep. 16, 2015

(86) PCT No.: PCT/US2015/050411
§ 371 (c)(1),
(2) Date: Mar. 16, 2017

(87) PCT Pub. No.: WO2016/044416
PCT Pub. Date: Mar. 24, 2016

(65) Prior Publication Data
US 2018/0187173 A1    Jul. 5, 2018

Related U.S. Application Data

(60) Provisional application No. 62/051,159, filed on Sep. 16, 2014.

(51) Int. Cl.
| | |
|---|---|
| A61K 48/00 | (2006.01) |
| C12N 9/22 | (2006.01) |
| C12N 5/0786 | (2010.01) |
| C12N 15/11 | (2006.01) |
| A61K 35/28 | (2015.01) |
| C12N 15/90 | (2006.01) |
| C07K 14/805 | (2006.01) |

(52) U.S. Cl.
CPC ............... *C12N 9/22* (2013.01); *A61K 35/28* (2013.01); *A61K 48/005* (2013.01); *C12N 5/0645* (2013.01); *C12N 15/11* (2013.01); *C12N 15/111* (2013.01); *C12N 15/907* (2013.01); *C07K 14/805* (2013.01); *C12N 2310/20* (2017.05); *C12N 2510/00* (2013.01); *C12N 2800/80* (2013.01)

(58) Field of Classification Search
USPC ....................................... 435/325; 424/93.21
See application file for complete search history.

(56) References Cited

U.S. PATENT DOCUMENTS

| | | |
|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,081 A | 10/2000 | Barbas |
| 6,140,466 A | 10/2000 | Barbas, III et al. |
| 6,174,670 B1 * | 1/2001 | Wittwer ............... B01L 3/5082 |
| 6,200,759 B1 | 3/2001 | Dove et al. |
| 6,242,568 B1 | 6/2001 | Barbas, III et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,607,882 B1 | 8/2003 | Cox, III et al. |
| 6,689,558 B2 | 2/2004 | Case |
| 6,794,136 B1 | 9/2004 | Eisenberg et al. |
| 6,824,978 B1 | 11/2004 | Cox, III et al. |
| 6,903,185 B2 | 6/2005 | Kim et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,153,949 B2 | 12/2006 | Kim et al. |
| 7,163,824 B2 | 1/2007 | Cox, III et al. |
| 7,253,273 B2 | 8/2007 | Collingwood |
| 7,262,054 B2 | 8/2007 | Jamieson et al. |
| 7,361,635 B2 | 4/2008 | Miller et al. |
| 7,807,464 B2 | 10/2010 | Zhang et al. |
| 7,888,121 B2 | 2/2011 | Urnov et al. |
| 7,914,796 B2 | 3/2011 | Miller et al. |
| 7,951,925 B2 | 5/2011 | Ando et al. |
| 7,972,854 B2 | 7/2011 | Miller et al. |

(Continued)

FOREIGN PATENT DOCUMENTS

| | | | |
|---|---|---|---|
| GB | 2338237 A | | 12/1999 |
| JP | WO2004/022743 | * | 3/2004 |

(Continued)

OTHER PUBLICATIONS

Chang (Blood, 2012, vol. 120, No. 19, p. 3906-3914).*

(Continued)

*Primary Examiner* — Michael C Wilson
(74) *Attorney, Agent, or Firm* — Pasternak Patent Law

(57) ABSTRACT

The present disclosure is in the field of genome engineering, particularly targeted modification of the genome of a hematopoietic stem cell.

9 Claims, 19 Drawing Sheets

Specification includes a Sequence Listing.

(56) References Cited

U.S. PATENT DOCUMENTS

| | | |
|---|---|---|
| 8,034,598 B2 | 10/2011 | Miller |
| 8,110,379 B2 | 2/2012 | DeKelver et al. |
| 8,168,428 B2 | 5/2012 | Zon et al. |
| 8,329,986 B2 | 12/2012 | Butler et al. |
| 8,409,861 B2 | 4/2013 | Guschin et al. |
| 8,563,314 B2 | 10/2013 | Gregory et al. |
| 8,586,526 B2 | 11/2013 | Gregory et al. |
| 8,623,618 B2 | 1/2014 | Doyon et al. |
| 8,697,359 B1 | 4/2014 | Zhang |
| 8,735,153 B2 | 5/2014 | Wolffe et al. |
| 8,741,640 B2 | 6/2014 | Gao et al. |
| 8,823,618 B2 | 9/2014 | Lee et al. |
| 8,932,814 B2 | 1/2015 | Cong et al. |
| 8,945,868 B2 | 2/2015 | Collingwood et al. |
| 8,956,828 B2 | 2/2015 | Bonini et al. |
| 9,005,973 B2 | 4/2015 | Cost et al. |
| 9,045,763 B2 | 6/2015 | DeKelver et al. |
| 2003/0232410 A1 | 12/2003 | Liljedahl et al. |
| 2005/0026157 A1 | 2/2005 | Baltimore et al. |
| 2005/0064474 A1 | 3/2005 | Urnov et al. |
| 2005/0208489 A1 | 9/2005 | Carroll et al. |
| 2005/0267061 A1 | 12/2005 | Martin |
| 2006/0063231 A1 | 3/2006 | Li et al. |
| 2006/0188987 A1 | 8/2006 | Guschin et al. |
| 2007/0218528 A1 | 9/2007 | Miller |
| 2008/0131962 A1 | 6/2008 | Miller |
| 2008/0159996 A1 | 7/2008 | Ando et al. |
| 2009/0054985 A1 | 2/2009 | Anderson |
| 2009/0068164 A1 | 3/2009 | Segal et al. |
| 2009/0305346 A1 | 12/2009 | Miller |
| 2010/0047805 A1 | 2/2010 | Wang |
| 2010/0218264 A1 | 8/2010 | Cui et al. |
| 2011/0207221 A1 | 8/2011 | Cost et al. |
| 2011/0265198 A1 | 10/2011 | Gregory et al. |
| 2012/0017290 A1 | 1/2012 | Cui et al. |
| 2013/0122591 A1 | 5/2013 | Cost et al. |
| 2013/0137104 A1 | 5/2013 | Cost et al. |
| 2013/0177960 A1 | 7/2013 | Regar |
| 2013/0177983 A1 | 7/2013 | Rebar |
| 2014/0080216 A1 | 3/2014 | Cost et al. |
| 2015/0056705 A1 | 2/2015 | Conway et al. |
| 2015/0335708 A1 | 11/2015 | Froelich et al. |

FOREIGN PATENT DOCUMENTS

| | | |
|---|---|---|
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 2007/014275 A2 | 2/2007 |
| WO | WO 2010/025421 A2 | 3/2010 |
| WO | WO 2010/079430 A1 | 7/2010 |
| WO | 2013019745 A1 | 2/2013 |
| WO | WO 2013/126794 A1 | 8/2013 |
| WO | 2013169398 A2 | 11/2013 |
| WO | WO 2014/015312 A1 | 1/2014 |
| WO | 2014036219 A2 | 3/2014 |

OTHER PUBLICATIONS

Wang (Cell Research, 2012, vol. 22, p. 637-648).*
Wayengera (BMC Blood Disorders, 2012, vol. 12, No. 5, p. 1-8).*
Ma (J. Biol. Chem., Nov. 29, 2013, vol. 288, No. 48, p. 34671-34679).*
Vannocci (J. Gene Med., Jan.-Feb. 2014, vol. 1-2, p. 1-10).*
Hoban (Mol. Therapy, May 2012, vol. 20, Supp 1, p. S122, #309).*
Dever (Nature, 2016, vol. 539, p. 384-389).*
Zou (Blood, 2011, vol. 118, No. 17, p. 4599-4608).*
Sabastiano (Stem Cells, 2011, vol. 29, p. 1717-1726).*
Andreani, et al., "Split Chimerism Between Nucleated and Red Blood Cells After Bone Marrow Transplantation for Haemoglobinopathies," Chimerism 2(1):21-22 (2011).
Baudet, et al., "RNAI Screen Identifies MAPK14 as a Druggable Supressor of Human Hematopoietic Stem Cell Expansion," Blood 119(26):6255-6258 (2012).
Beerli, et al., "Engineering Polydactyl Zinc-Finger Transcription Factors," Nature Biotechnology 20:135-141 (2002).
Boch, et al., "Breaking the Code of DNA Binding Specificity of TAL-Type III Effectors," Science 326:1509-1512 (2009).
Boitano, et al., "Aryl Hydrocarbon Receptor Antagonists Promote the Expansion of Human Hematopoietic Stem Cells," Science 329(5997):1345-1348 (2010).
Bonas, et al., "Genetic and Structural Characeterization of the Avirulence Gene AVRBS3 From Xanthomonas Campestris PV. Vesicatoria," Mol Gen Genet 218:127-136 (1989).
Breems, et al., "Stroma-Contact Prevents Loss of Hematopoietic Stem Cell Quality During Ex Vivo Expansion of CD341 Mobilized Peripheral Blood Stem Cells," Blood 91(1):111-117 (1998).
Buechele, et al., "MLL Leukemia Induction by Genome Editing of Human CD34+ Hematopoietic Cells," Blood 126(14):1683-1694 (2015).
Butler, et al., "Development of a Vascular Niche Platform for Expansion of Repopulating Human Cord Blood Stem and Progenitor Cells," Blood. 120(6):1344-1347 (2012).
Challita, P. M., et al., "Multiple Modifications in CIS Elements of the Long Terminal Repeat of Retroviral Vectors Lead to Increased Expression and Decreased DNA Methylation in Embryonic Carcinoma Cells," J of Virol 69:748-755 (1995).
Chandrakasan, et al., "Gene Therapy for Hemoglobinopathies: The State of the Field and the Future," Hematol Oncol Clin of North Amer 28(2):199-216 (2014).
Chaurasia, et al., "Epigenetic Reprogramming Induces the Expansion of Cord Blood Stem Cells," Journal of Clinical Investigation 124(6):2378-2395 (2014).
Choo, et al., "Advances in Zinc Finger Engineering," Current Opinion in Structural Biology 10:411-416 (2000).
Christian, et al., "Targeting DNA Double-Strand Breaks With TAL Effector Nucleases," Genetics 186:757-761, DOI: 10.1534/genetics.110.120717 (2010).
Cong, et al., "Multiplex Genome Engineering Using CRISPR/CAS Systems," Science 339(6121):819-823, DOI: 10.1126/science.1231143 (2013).
De Lima, et al., "Transplantation of Ex Vivo Expanded Cord Blood Cells Using the Copper Chelator Tetraethylenepentamine: A Phase I/II Clinical Trial," Bone Marrow Transplantation 41:771-778 (2008).
Dull, et al., "A Third-Generation Lentivirus Vector With a Conditional Packaging System," Journal of Virology 72(11):8463-8471 (1998).
Fares, et al., "UM171 is a Novel and Potent Agonist of Human Hematopoietic Stem Cell Renewal," Blood 122(21):798 (2013).
Follenzi, et al., "Gene Transfer by Lentiviral Vectors Is Limited by Nuclear Translocation and Rescued by HIV-1 POL Sequences," Nature Genetics 25:217-222 (2000).
Gabriel, R., et al., "An Unbiased Genome-Wide Analysis of Zinc-Finger Nuclease Specificity," Nat Biotech 29(9):816-823 (2011).
Gaj, et al., "ZFN, TALEN, and CRISPR/CAS-Based Methods for Genome Engineering," Trends in Biotechnology 31(7):397-405 (2013).
Genovese, et al., "Targeted Genome Editing in Human Repopulating Haematopoietic Stem Cells," Nature 510:235-240 (2014).
Giarratana, et al., "Ex Vivo Generation of Fully Mature Human Red Blood Cells From Hematopoietic Stem Cells," Nat Biotech 23:69-74 (2005).
Giarratana, M., et al., "Proof of Principle for Transfusion of In Vitro-Generated Red Blood Cells," Blood 118:5071-5079 (2011).

(56) References Cited

OTHER PUBLICATIONS

Guo, et al., "Directed Evolution of an Enhanced and Highly Efficient FOKI Cleavage Domain for Zinc Finger Nucleases," *J. Mol. Biol.* 400(1):96-107 (2010).
Haft, et al., "A Guild of 45 CRISPR-Associated (CAS) Protein Families and Multiple CRISPR/CAS Subtypes Exist in Prokaryotic Genomes," *PLoS Computational Biology* 1(6):e60 (2005).
Heuer, et al., "Repeat Domain Diversity of AVRBS3-Like Genes in Ralstonia Solanacearum Strains and Association With Host Preferences in the Field," *Applied and Environmental Microbiology* 73(13):4379-4384 (2007).
Holt, et al., "Zinc Finger Nuclease-Mediated CCR5 Knockout Hematopoietic Stem Cell Transplantation Controls HIV-1 In Vivo," *Nat Biotechnol.* 28(8)839-847, doi:10.1038/nbt.1663 (2010).
Horwitz, et al., "Umbilical Cord Blood Expansion With Nicotinamide Provides Long-Term Multilineage Engraftment," *Journal of Clinical Investigation* 124(7):3121-3128 (2014).
Isalan, et al., "A Rapid, Generally Applicable Method to Engineer Zinc Fingers Illustrated by Targeting the HIV-1 Promoter," *Nat Biotechnol.* 19(7):656-660 (2001).
Jansen, et al., "Identification of Genes That Are Associated With DNA Repeats in Prokaryotes," *Molecular Microbiology* 43(6):1565-1575 (2002).
Jinek, et al., "A Programmable Dual-RNA-Guided DNA Endonuclease in Adaptive Bacterial Immunity," *Science* 337:816-821 (2012).
Jinek, et al., "RNA-Programmed Genome Editing in Human Cells," *eLife* 2:e00471. DOI: 10.7554/eLife.00471 (2013).
Joglekat, et al., "Integrase-Defective Lentiviral Vectors as a Delivery Platform for Targeted Modification of Adenosine Deaminase Locus," *Mol. Ther.: J of the Amer Soc Gene Ther* 21:1705-17 (2013).
Kay, et al., "A Bacterial Effector Acts as a Plant Transcription Factor and Induces a Cell Size Regulator," *Science* 318:648-651 (2007).
Kim, et al., "Chimeric Restriction Endonuclease," *Proc. Natl. Acad. Sci. USA* 91:883-887 (1994).
Kim, et al., "Insertion and Deletion Mutants of FOKI Restriction Endonuclease," *Journal Biological Chemistry* 269(50):31978-31982 (1994).
Li, et al., "Functional Domains in FOK I Restriction Endonuclease," *Proc. Natl. Acad. Sci USA* 89:4275-4279 (1992).
Li, et al., "Alteration of the Cleavage Distance of FOK I Restriction Endonuclease by Insertion Mutagenesis," *Proc. Natl. Acad. Sci USA* 90:2764-2768 (1993).
Magin, et al., "Primary Cells as Feeder Cells for Coculture Expansion of Human Hematopoietic Stem Cells From Umbilical Cord Blood—A Comparative Study," *Stem Cells and Development* 18(1):173-186 (2009).
Makarova, et al., "A DNA Repair System Specific for Thermophilic Archaea and Bacteria Predicted by Genomic Context Analysis," *Nucleic Acids Research* 30(2):482-496 (2002).
Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biology Direct* 1:7 (2006).
Mohrin, et al., "Hematopoietic Stem Cell Quiescence Promotes Error Prone DNA Repair and Mutagenesis," *Cell Stem Cell* 7:174-185 (2010).
Moscou, et al., "A Simple Cipher Governs DNA Recognition by TAL Effectors," *Science* 326:1501 (2009).
Naldini, et al., "Efficient Transfer, Integration, and Sustained Long-Term Expression of the Transgene in Adult Rat Brains Injected With a Lentiviral Vector," *Proc. Natl/ Acad. Sci. USA* 93:11382-11388 (1996).
North, et al., "Prostaglandin E2 Regulates Vertebrate Haematopoietic Stem Cell Homeostasis," *Nature* 447(7147):1007-1011 (2007).
Olovnikov, et al., "Bacterial Argonaute Samples the Transcriptome to Identify Foreign DNA," *Molecular Cell* 51:594-605 (2013).
Pabo, et al., "Design and Selection of Novel CYS2-HIS2 Zinc Finger Proteins," *Ann. Rev. Biochem.* 70:313-340 (2001).
Pabst, et al., "Identification of Small Molecules That Support Human Leukemia Stem Cell Activity Ex Vivo," *Nature Methods* 11(4):436-442 (2014).
Perez, et al., "Establishment of HIV-1 Resistance in CD4+ T Cells by Genome Editing Using Zinc-Finger Nucleases," *Nature Biotechnology* 26(7):808-816 (2008).
Romero, et al., "β-Globin Gene Transfer to Human Bone Marrow for Sickle Cell Disease," *J Clin Invest* 123(8):3317-3330 (2013).
Schornack, et al., "Gene-for-Gene-Mediated Recognition of Nuclear-Targeted AVRBS3-Like Bacterial Effector Proteins," *Journal of Plant Physiology* 163(3):256-272 (2006).
Segal, et al., "Custom DNA-Binding Proteins Come of Age: Polydactyl Zinc-Finger Proteins," *Current Opinion Biotechnology* 12:632-637 (2001).
Sheng, et al., "Structure-Based Cleavage Mechanism of Thermus Thermophilus Argonaute DNA Guide Strand-Mediated DNA Target Cleavage," *Proc. Natl. Aca. Sci. U.S.A.* 111(2):652-657 (2014).
Stella, et al., "CD34-Positive Cells: Biology and Clinical Relevance," *Hematologica* 80:367-387 (1995).
Swarts, et al., "DNA-Guided DNA Interference by a Prokaryotic Argonaute," *Nature* 507(7491):258-261 doi:10.1038/nature12971 (2014).
Tebas, et al., "Gene Editing of CCR5 in Autologous CD4 T Cells of Persons Infected With HIV," *The New England Journal of Medicine* 370(10):901 (2014).
Urnov, et al., "Highly Efficient Endogenous Human Gene Correction Using Designed Zinc-Finger Nucleases," *Nature* 435(7042):646-651 (2005).
Vogel, "A Bacterial Seek-and-Destroy System for Foreign DNA," *Science* 344(6187):972-973 (2014).
Voon, et al., "Apoptotic Pathways to Death in Myelodysplastic Syndromes," *Haematologica* 93(8):1288(2008).
Walters, et al., "Stable Mixed Hematopoietic Chimerism After Bone Marrow Transplantation for Sickle Cell Anemia," *American Society for Blood and Marrow Transplantation* 7:665-673 (2001).
Wang, et al., "Rapamycin Relieves Lentiviral Vector Transduction Resistance in Human and Mouse Hematopoietic Stem Cells," *Blood* 124(6):913-923 (2014).
Watts, et al., "Hematopoietic Stem Cell Expansion Facilitates Multilineage Engraftment in a Nonhuman Primate Cord Blood Transplantation Model," *Exp Hematol* 40(3):187-196 (2012).
Wilbur, A., et al., "Therapeutic Levels of Fetal Hemoglobin in Erythroid Progeny of β-Thalassemic CD3411 Cells After Lentiviral Vector-Mediated Gene Transfer," *Blood* 117:2817-2826 (2011).
Yuan, et al., "Crystal Structure of A. Aeolicus Argonaute, a Site-Specific DNA-Guided Endoribonuclease, Provides Insights Into RISC-Mediated mRNA Cleavage," *Molecular Cell* 19:405-419 (2005).
Zhang, et al., "Angiopoietin-Like 5 and IGFBP2 Stimulate Ex Vivo Expansion of Human Cord Blood Hematopoietic Stem Cells as Assayed by NOD/SCID Transplantation," *Blood.* 111(7):3415-3423 (2008).
Zuffery, et al., "Self-Inactivating Lentivirus Vector for Safe and Efficient In Vivo Gene Delivery," *Journal of Virology* 72(12):9873-9880 (1998).

\* cited by examiner

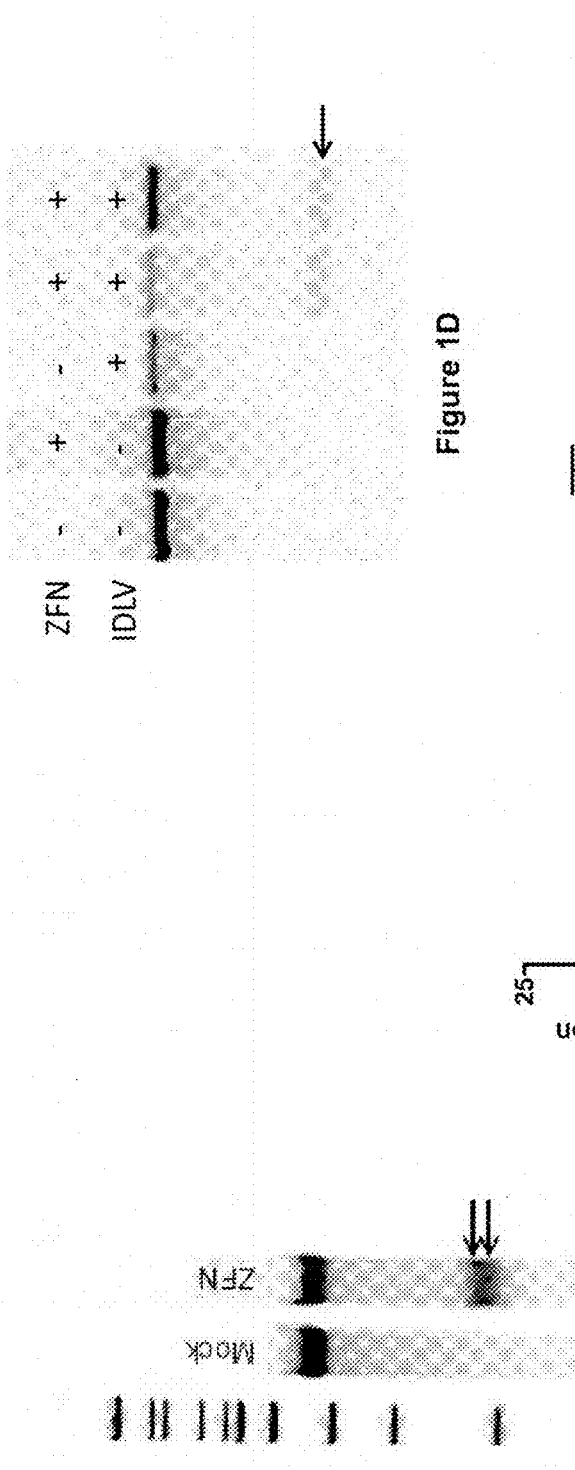
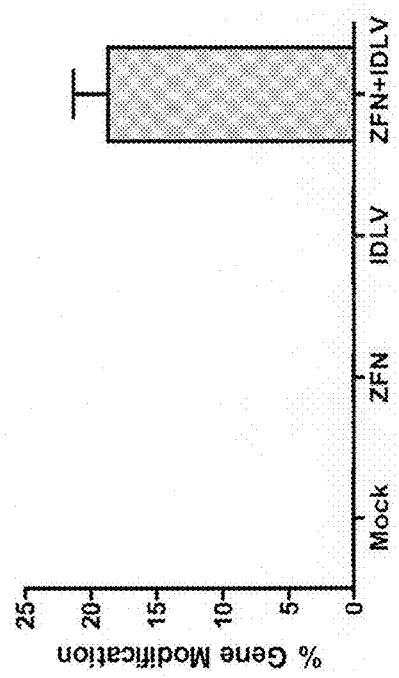
Figure 1A
5'-TCAAACAGACACCATGGTGCATCTGACTCCTGAGGAGAAGTCTGCCGTTACTGCCCTGTGGGC
Figure 1B
Figure 1D
Figure 1E

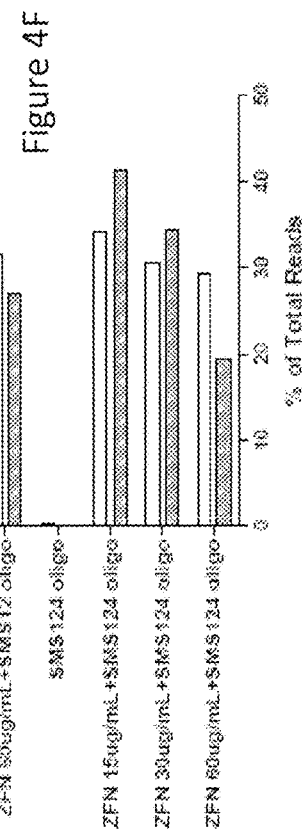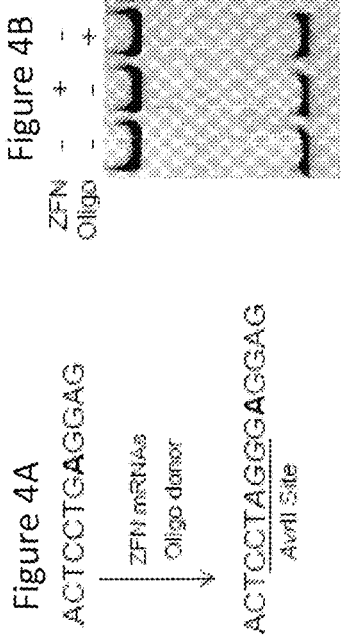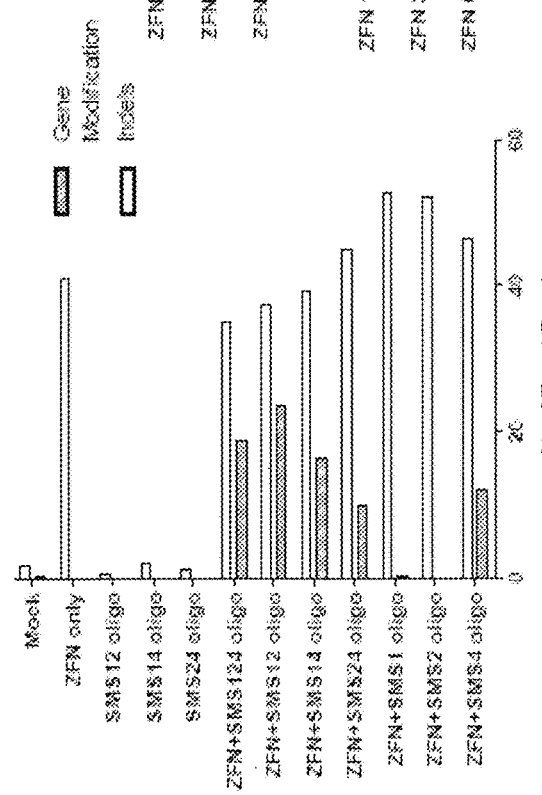

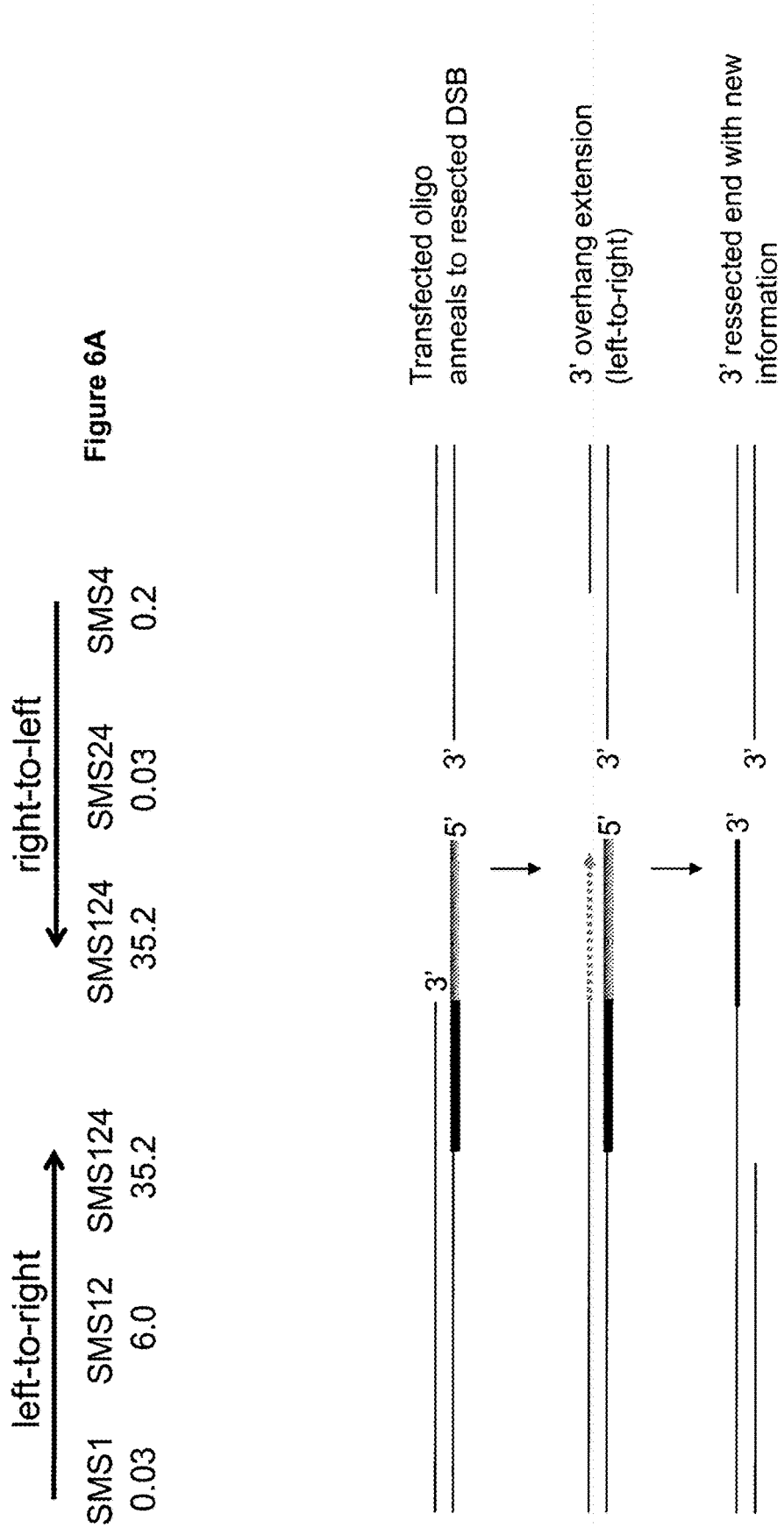

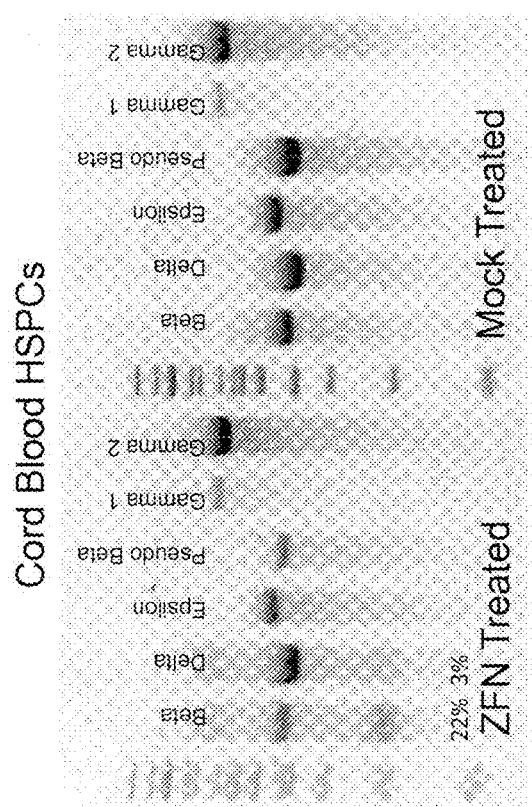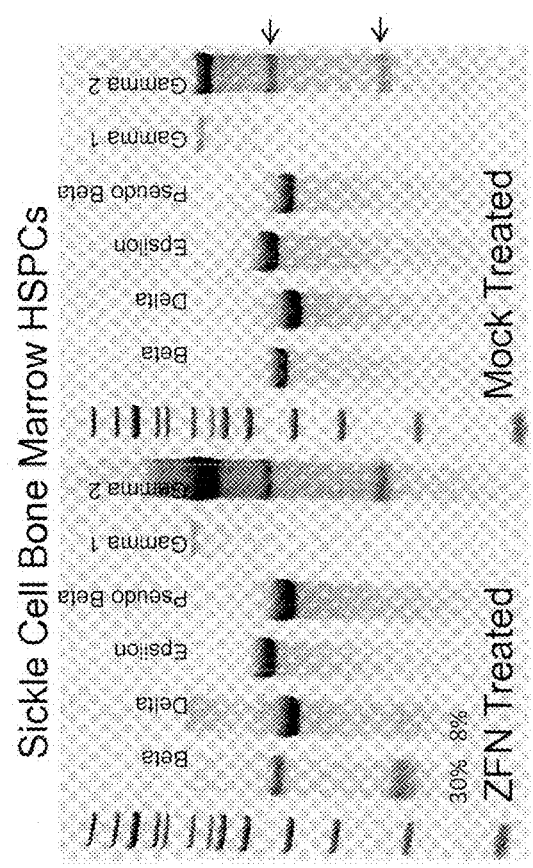

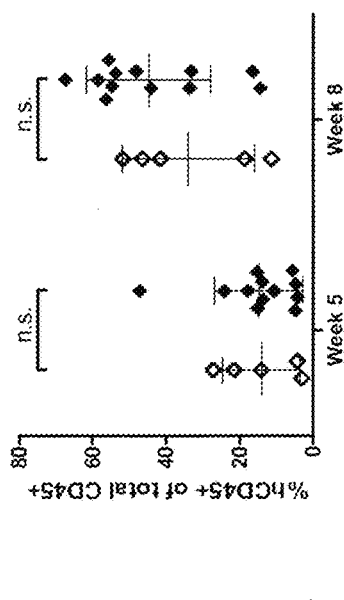
Figure 10C
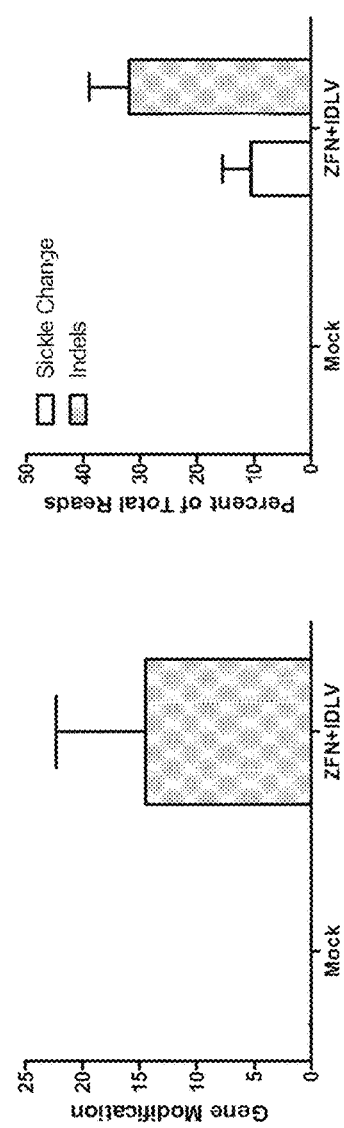
Figure 10A
Figure 10B
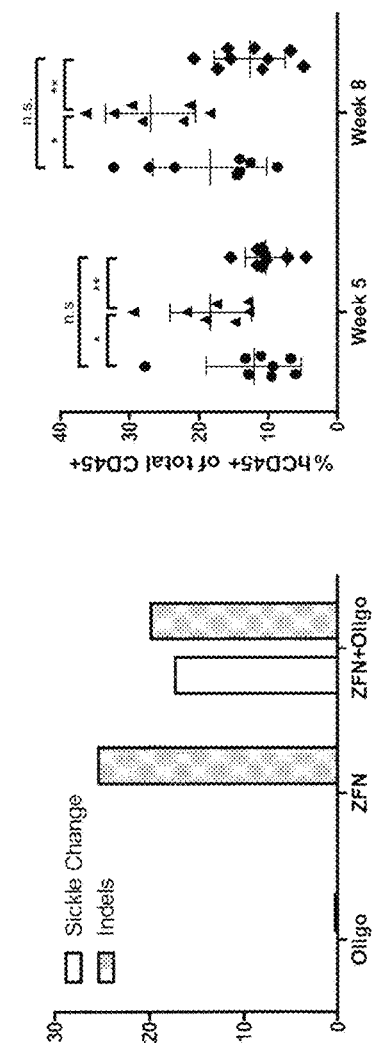
Figure 10D
Figure 10E

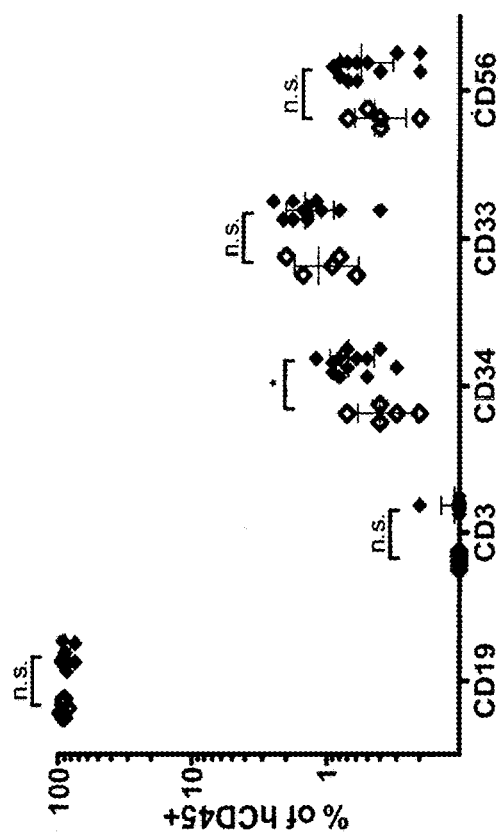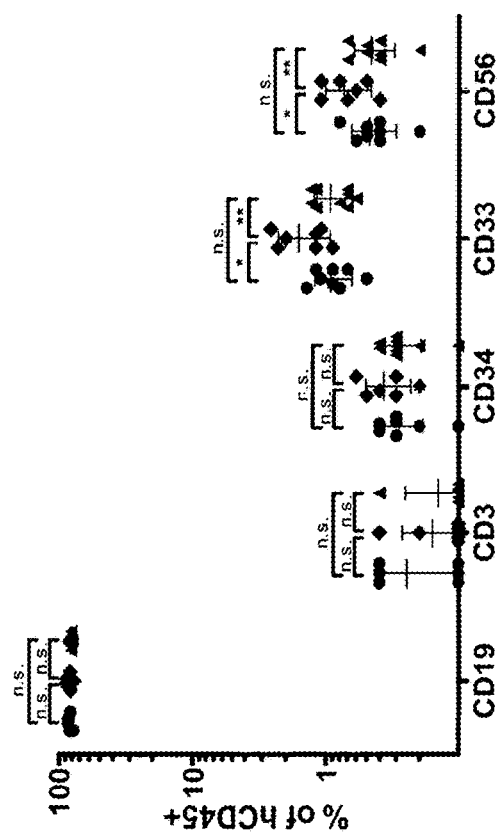

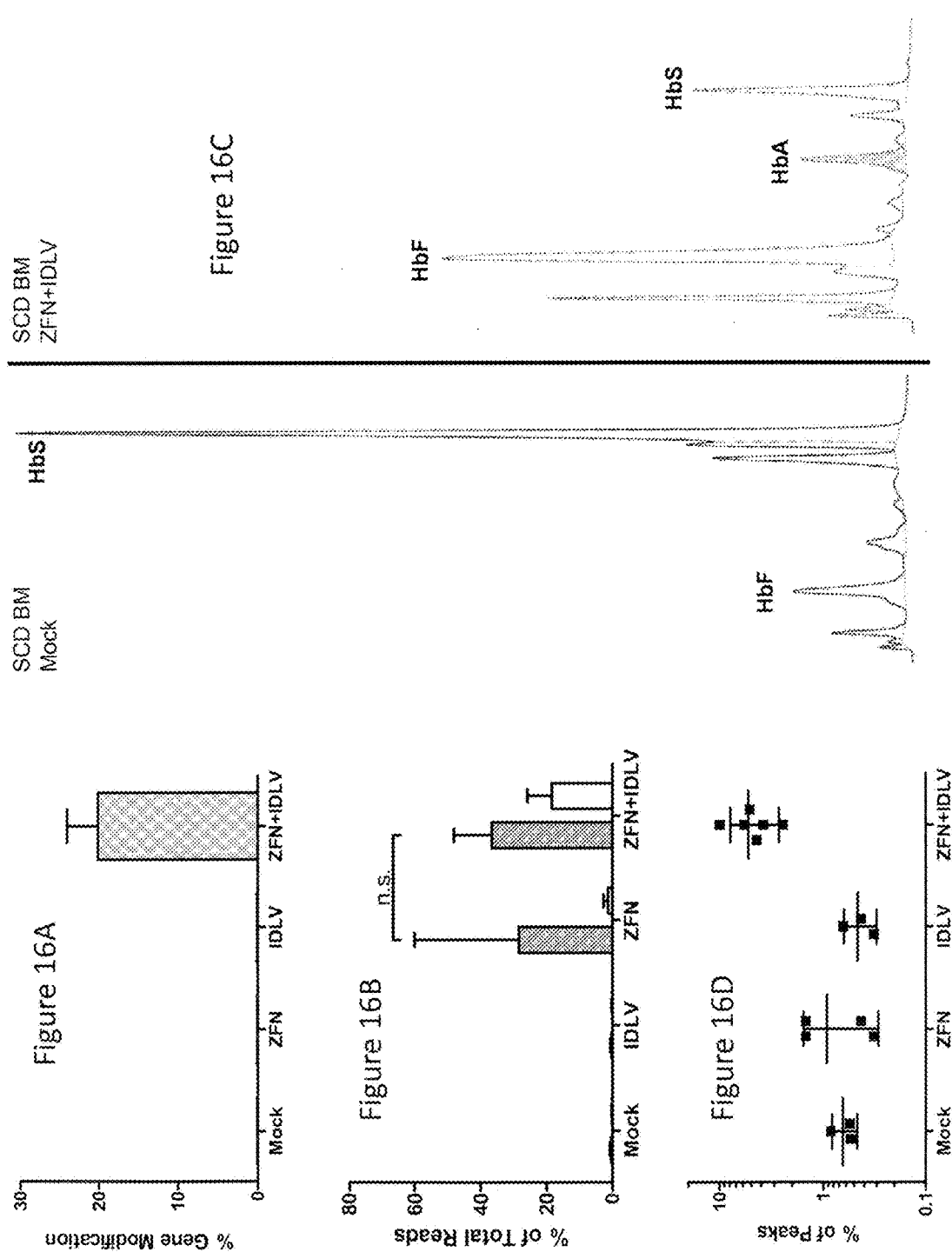

GENETICALLY MODIFIED HUMAN CELL WITH A CORRECTED MUTANT SICKLE CELL MUTATION

CROSS-REFERENCE TO RELATED APPLICATIONS

This application is a 35 U.S.C. § 371 filing of PCT/US2015/050411, filed Sep. 16, 2015, which claims the benefit of U.S. Provisional Application No. 62/051,159 filed Sep. 16, 2014, the disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Mar. 16, 2017, is named 83280127SL.txt and is 15,726 bytes in size.

TECHNICAL FIELD

The present disclosure is in the field of genome engineering, particularly targeted modification of the genome of a hematopoietic cell.

BACKGROUND

One of the most promising approaches in the gene therapy for a large number of diseases involves the use of in vitro genetic modification of stem cells followed by transplantation and engraftment of the modified cells in a patient. Particularly promising is when the introduced stem cells display long term persistence and multi-lineage differentiation. Hematopoietic stem cells, most commonly in the form of cells enriched based on the expression of the CD34 cell surface marker, are a particularly useful cell population since they can be easily obtained and contain the long term hematopoietic stem cells (LT-HSCs), which can reconstitute the entire hematopoietic lineage after transplantation.

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus in cells from any organism. See, e.g., U.S. Pat. Nos. 9,045,763; 9,005,973; 8,956,828; 8,945,868; 8,586,526; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410; 20050208489; 20050026157; 20050064474; 20060063231; 20080159996; 201000218264; 20120017290; 20110265198; 20130137104; 20130122591; 20130177983; 20130177960; 20150056705; and 20150335708, the disclosures of which are incorporated by reference in their entireties for all purposes. These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). The repair pathway followed (NHEJ versus HDR or both) typically depends on the presence of a repair template and the activity of several competing repair pathways.

Introduction of a double strand break in the absence of an externally supplied repair template (e.g. donor) is commonly used for the inactivation of the targeted gene via mutations introduced by the cellular NHEJ pathway. NHEJ pathways can be separated into the standard Ku-dependent pathway and an alternative Ku-independent pathway based on microhomology-mediated end joining, which takes advantage of short tracks of direct repeats near the cleavage site. The pattern of insertions and/or deletions ('indels') following gene editing via these two NHEJ pathways differ, which can result in differences in the functional consequences of the mutations, depending on the application.

In the presence of an externally supplied donor carrying stretches of homology to the sequences flanking the double strand break, homology directed gene repair (HDR) using the donor molecule can be used to change the sequence of a single base or a small stretch of DNA ('gene correction') or, on the other extreme, for the targeted insertion of an entire expression cassette ('gene addition') into a predetermined genomic location.

Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage. See, e.g., U.S. Pat. Nos. 8,697,359 and 8,932,814 and U.S. Patent Publication No. 20150056705. Further, targeted nucleases are being developed based on the Argonaute system (e.g., from *T. thermophilus*, known as 'TtAgo', see Swarts et al (2014) *Nature* 507(7491): 258-261), which also may have the potential for uses in genome editing and gene therapy.

Targeted cleavage using one of the above mentioned nuclease systems can be exploited to insert a nucleic acid into a specific target location using either HDR or NHEJ-mediated processes. However, delivering both the nuclease system and the donor to the cell can be problematic. For example, delivery of a donor or a nuclease via transduction of a plasmid into the cell can be toxic to the recipient cell, especially to a cell which is a primary cell and so not as robust as a cell from a cell line.

CD34+ stem or progenitor cells are a heterogeneous set of cells characterized by their ability to self-renew and/or differentiate into the cells of the lymphoid lineage (e.g. T cells, B cells, NK cells) and myeloid lineage (e.g. monocytes, erythrocytes, eosinophils, basophils, and neutrophils). Their heterogeneous nature arises from the fact that within the CD34+ stem cell population, there are multiple subgroups which often reflect the multipotency (whether lineage committed) of a specific group. For example, CD34+ cells that are CD38− are more primitive, immature CD34+ progenitor cell, (also referred to as long term hematopoietic progenitors), while those that are CD34+CD38+ (short term hematopoietic progenitors) are lineage committed (see Stella et al (1995) *Hematologica* 80:367-387). When this population then progresses further down the differentiation pathway, the CD34 marker is lost. CD34+ stem cells have enormous potential in clinical cell therapy.

Red blood cells (RBCs), or erythrocytes, are the major cellular component of blood. In fact, RBCs account for one quarter of the cells in a human. Mature RBCs lack a nucleus and many other organelles in humans, and are full of hemoglobin, a metalloprotein found in RBCs that functions to carry oxygen to the tissues as well as carry carbon dioxide out of the tissues and back to the lungs for removal. The protein makes up approximately 97% of the dry weight of RBCs and it increases the oxygen carrying ability of blood by about seventy fold. Hemoglobin is a heterotetramer comprising two α-like globin chains and two β-like globin chains and 4 heme groups. In adults the α2β2 tetramer is referred to as Hemoglobin A (HbA) or adult hemoglobin. Typically, the alpha and beta globin chains are synthesized in an approximate 1:1 ratio and this ratio seems to be critical in terms of hemoglobin and RBC stabilization. In fact, in some cases where one type of globin gene is inadequately expressed (see below), reducing expression (e.g. using a specific siRNA) of the other type of globin, restoring this 1:1 ratio, alleviates some aspects of the mutant cellular phenotype (see Voon et al (2008) *Haematologica* 93(8):1288). In a developing fetus, a different form of hemoglobin, fetal hemoglobin (HbF) is produced which has a higher binding affinity for oxygen than Hemoglobin A such that oxygen can be delivered to the baby's system via the mother's blood stream. Fetal hemoglobin also contains two α globin chains, but in place of the adult β-globin chains, it has two fetal γ-globin chains (i.e., fetal hemoglobin is α2γ2). At approximately 30 weeks of gestation, the synthesis of γ globin in the fetus starts to drop while the production of β globin increases. By approximately 10 months of age, the newborn's hemoglobin is nearly all α2β2 although some HbF persists into adulthood (approximately 1-3% of total hemoglobin). The regulation of the switch from production of γ to β is quite complex, and primarily involves an expressional down-regulation of γ globin with a simultaneous up-regulation of β globin expression.

Genetic defects in the sequences encoding the hemoglobin chains can be responsible for a number of diseases known as hemoglobinopathies, including sickle cell anemia and thalassemias. In the majority of patients with hemoglobinopathies, the genes encoding γ globin remain present, but expression is relatively low due to normal gene repression occurring around parturition as described above.

It is estimated that 1 in 5000 people in the U.S. have sickle cell disease (SCD), mostly in people of sub-Saharan Africa descent. There appears to be a benefit of sickle cell heterozygosity for protection against malaria, so this trait may have been selected for over time, such that it is estimated that in sub-Saharan Africa, one third of the population has the sickle cell trait. Sickle cell disease is caused by a mutation in the β-globin gene in which valine is substituted for glutamic acid at amino acid #6 (a GAG to GTG at the DNA level), where the resultant hemoglobin is referred to as "hemoglobin S" or "HbS." Under lower oxygen conditions, a conformational shift in the deoxy form of HbS exposes a hydrophobic patch on the protein between the E and F helices. The hydrophobic residues of the valine at position 6 of the beta chain in hemoglobin are able to associate with the hydrophobic patch, causing HbS molecules to aggregate and form fibrous precipitates. These aggregates in turn cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of γ globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thus, there remains a need for additional methods and compositions that can be used for genome editing, to correct an aberrant gene or alter the expression of others for example to treat hemoglobinopathies such as sickle cell disease.

SUMMARY

Disclosed herein are methods and compositions for altering the expression or for correcting one or more genes encoding proteins involved in a genetic disease (e.g., producing proteins lacking, deficient or aberrant in the disease and/or proteins that regulate these proteins) such as sickle cell disease. The present invention describes compositions and methods for use in gene therapy and genome engineering.

Alteration of such proteins can result in the treatment of these genetic diseases. In particular, genome editing is used to correct an aberrant gene, insert a wild type gene, or change the expression of an endogenous gene. One approach involves the use of gene correction where a faulty endogenous β globin gene is targeted and the mutant sequence replaced. One approach further involves the use of modification of a stem cell (e.g., hematopoietic stem cell or RBC precursor), which stem cell can then be used to engraft into a patient, for treatment of a hemoglobinopathy.

In one aspect, described herein is a genetically modified cell or cell line, for example as compared to the wild-type genomic sequence of the same type of cell or cell line. In certain embodiments, the cells comprise genetically modified RBC precursors (hematopoietic stem cells known as "HSCs"). The cell or cell line may be heterozygous or homozygous for the modification. The modifications may comprise insertions, deletions and/or combinations thereof. In certain embodiments, the HSCs are modified with an engineered nuclease and a donor nucleic acid such that a wild type gene (e.g., globin gene) is inserted and expressed and/or an endogenous aberrant gene is corrected. In certain embodiments, the modification (e.g., insertion) is at or near the nuclease(s) binding and/or cleavage site(s), including but not limited to, modifications to sequences within 1-300 (or any number of base pairs therebetween) base pairs upstream or downstream of the site(s) of cleavage and/or binding site; modifications within 1-100 base pairs (or any number of base pairs therebetween) of either side of the binding and/or cleavage site(s); modifications within 1 to 50 base pairs (or any number of base pairs therebetween) on either side of the binding and/or cleavage site(s); and/or modifications to one or more base pairs of the nuclease binding site and/or cleavage site. In certain embodiments, the modification is at or near (e.g., 1-300 base pairs or any number of base pairs therebetween) SEQ ID NO:23 or 24. In other embodiments, the modification is 1-100 (or any number of base pairs therebetween) base pairs of SEQ ID NO:23 or 24. In certain embodiments, the modification is within SEQ ID NO:23 and/or SEQ ID NO:24, for example a modification of 1 or more base pairs in either SEQ ID NO:23 or 24. In some cases, the wild type gene sequence for insertion encodes a wild type β globin. In other cases, the endogenous aberrant gene is the β globin gene, for example one or more genomic modifications that correct at least one mutation in an endogenous aberrant human beta-hemoglobin (Hbb) gene. In some aspects, the modification of the beta globin gene allows proper splicing of transcribed RNAs. In other aspects, the modification of the beta globin gene corrects the mutation in the sickle allele such that codon GTG that codes for the incorrect valine amino acid at the sixth position in the polypeptide sequence is altered to GAG, encoding glutamic acid as is found in the wild type polypeptide. Partially or fully differentiated cells descended from the genetically modified stem cells as described herein are also provided (e.g., RBCs or RBC precursor cells). Compositions such as pharmaceutical compositions comprising the genetically modified cells as described herein are also provided.

In another aspect, described herein is a zinc-finger protein (ZFP) that binds to target site in a region of interest (e.g., a β globin gene) in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a globin or safe harbor gene. In certain embodiments, the zinc finger domain comprises 5 or 6 zinc finger domains and recognizes a target site in a globin gene (e.g., a zinc finger protein having 5 or 6 fingers with the recognition helix regions shown in Table 1).

In another aspect, described herein is a TALE protein (Transcription activator like) that binds to target site in a region of interest (e.g., β globin gene) in a genome, wherein the TALE comprises one or more engineered TALE binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I).

In another aspect, described herein is a CRISPR/Cas or a TtAgo system that binds to target site in a region of interest (e.g., a disease associated gene) in a genome, wherein the CRISPR/Cas system comprises a CRIPSR/Cas nuclease and an engineered crRNA/tracrRNA (or single guide RNA). In certain embodiments, the CRISPR/Cas or the TtAgo system recognizes a target in a globin gene.

In some embodiments, the nuclease which facilitates genomic engineering of the cell is delivered as a peptide, while in others it is delivered as a nucleic acid encoding the nuclease. In some embodiments, more than one nuclease is used and may be delivered in nucleic acid form, protein form, or combinations thereof. In some preferred embodiments, the nucleic acid(s) encoding the nuclease is (are) an mRNA, and in some instances, the mRNA is protected. In further preferred embodiments, the mRNA may comprise an ARCA cap and/or may comprise a mixture of modified and unmodified nucleotides. The nuclease may comprise a zinc finger nuclease (ZFN), a TALE-nuclease (TALEN), TtAgo or a CRISPR/Cas nuclease system or a combination thereof. In a preferred embodiment, the nucleic acid encoding the nuclease(s) is delivered via electroporation. In another aspect, described herein is a method for increasing targeted integration (e.g., via HDR) following nuclease-mediated cleavage in a cell. In certain embodiments, the methods comprise the steps of: (i) introducing one or more nucleases (and/or mRNAs or expression constructs that express the nuclease(s) and one or more single guide RNA if needed) along with one or more donor molecules into a host cell and (ii) introducing one or more factors that affect and/or increase stem cell expansion without loss of sternness or differentiation into the cell and/or the culture media containing the cell before, during and/or after introduction of the nuclease(s). The donor may be delivered prior to, after, or along with the nucleic acid encoding the nuclease(s).

The donor can be delivered by viral and/or non-viral gene transfer methods. In other embodiments, the donor is delivered to the cell via an adeno associated virus (AAV). In some instances, the AAV comprises LTRs that are of a heterologous serotype in comparison with the capsid serotype. In other embodiments, the donor is delivered to the cell via a lentivirus. In some instances, the lentivirus is an integrase defective lentivirus (IDLV).

In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In yet further embodiments, the DSB is created using a CRISPR/Cas nuclease system where an engineered single guide RNA or its functional equivalent is used to guide the nuclease to a targeted site in a genome. In yet further embodiments, the DSB is created using a TtAgo system.

In another aspect, the invention provides kits that are useful for increasing gene disruption and/or targeted integration (e.g. gene correction) following nuclease-mediated cleavage of a cell's genome (e.g. ZFNs, TAL-effector domain nuclease fusion proteins, a TtAgo system, or engineered homing endonucleases or engineered guide RNAs with the CRISPR/Cas system). The kits typically include one or more nucleases that bind to a target site, one or more factors that affect stem cell expansion and/or differentiation and instructions for introducing the nucleases and stem cell-affecting factors into the cells such that nuclease-mediated gene disruption and/or targeted integration is enhanced. Optionally, cells containing the target site(s) of the nuclease may also be included in the kits described herein. In certain embodiments, the kits comprise at least one construct with the target gene and a known nuclease capable of cleaving within the target gene. Such kits are useful for optimization of cleavage conditions in a variety of varying host cell types. Other kits contemplated by the invention may include a known nuclease capable of cleaving within a known target locus within a genome, and may additionally comprise a donor nucleic acid. In some aspects, the donor DNA may encode a polypeptide, a regulatory region or a structural nucleic acid. In some embodiments, the polypeptide is a reporter gene (e.g. GFP). Such kits are useful for optimization of conditions for donor integration or for the construction of specifically modified cells, cell lines, and animals containing gene disruptions or targeted insertions.

In other aspects, methods of administering a genetically modified stem cell as described herein to a subject are described. The genetically modified blood cell precursors ("HSC/PC") as described herein are typically given in a bone marrow transplant and the HSC/PC differentiate and mature in vivo. In some embodiments, the HSC/PC are isolated following G-CSF-induced mobilization, and in others, the cells are isolated from human bone marrow or umbilical cords. In some aspects, the HSC/PC are edited by treatment with a nuclease designed to knock out a specific gene or regulatory sequence. In other aspects, the HSC/PC are modified with an engineered nuclease and a donor nucleic acid such that a wild type gene or other gene of interest is inserted and expressed and/or an endogenous aberrant gene is corrected. In some embodiments, the modified HSCs/PC are administered to the patient following mild myeloablative pre-conditioning. In other aspects, the HSC/PC are administered after full myeloablation such that following engraftment, 100% of the hematopoietic cells are derived from the modified HSC/PC. Furthermore, the cell may be arrested in the G2 phase of the cell cycle.

In some embodiments, the transgenic HSC/PC cell and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

These and other aspects will be readily apparent to the skilled artisan in light of disclosure as a whole.

BRIEF DESCRIPTION OF THE DRAWINGS

FIGS. 1A through 1E show cleavage and correction at the beta-globin locus in CD34+ cells using an IDLV donor. FIG. 1A (SEQ ID NO:3) shows a portion of exon I DNA sequence of beta-globin showing the ZFN target sites (underlined) atop the start codon (bold) and the sickle mutation (bold, italic). FIG. 1B is a gel showing targeted cleavage at the beta-globin locus in human umbilical cord blood CD34+ cells. Cells were analyzed three days after electroporation with in vitro transcribed mRNA encoding the ZFNs. 'Mock' represents untreated CD34+ cells. Arrows indicate cut bands following PCR amplification and digestion with Surveyor® Nuclease (Transgenomic®). FIG. 1C is a schematic of site-specific gene correction at the sickle mutation in the beta globin gene relative to exons 1 and 2. Also illustrated are details of the donor construct and resulting genomic DNA upon cleavage by ZFNs and repair by HDR. Location of sickle mutation and HhaI RFLP (asterisk) indicated. Primer locations for Surveyor Nuclease and RFLP assays shown underneath. Exons to scale; angled hash marks indicate areas not to scale. FIG. 1D is a RFLP gel for targeted gene modification of beta-globin in the presence of the ZFNs and donor. Cord blood (CB) CD34+ cells were electroporated with in vitro transcribed ZFN mRNA and/or transduced with donor comprising IDLV as indicated at the top of the gel. Cells were harvested four days after treatment, PCR amplified from outside the donor region, digested with HhaI enzyme, and resolved on an agarose gel. The arrow shows the cleaved product, indicating incorporation of the RFLP into the genome at the target site. FIG. 1E is a graph showing gene modification percentages in CD34+ cells under the indicated conditions. CB CD34+ cells were electroporated with in vitro transcribed ZFN mRNA and transduced with donor IDLV. Cells were harvested three days after treatment, PCR amplified from outside the donor region and qPCR was completed with primers designed to specifically detect the incorporation of the silent base change generating the HhaI RFLP and normalized to primers binding in Exon 2 of the beta-globin locus in the amplicon, (n=4 for all conditions). Gene modification was found in approximately 18% of cells treated with both ZFNs and donor.

FIGS. 2A, B and C are graphs showing results following titration of the ZFN mRNA. CD34+ cells were electroporated with increasing amounts of in vitro transcribed ZFN mRNA and transduced with a constant amount of donor IDLV. Mock indicates untreated cells, ZFN only sample electroporated with 30 ug/mL of each ZFN, IDLV only sample pulsed and transduced with 2E+07 TU/ml of donor IDLV. FIG. 2A shows gene modification rates at 3 days post electroporation as determined by qPCR for the RFLP. FIG. 2B shows fold expansion at 1 day post electroporation and FIG. 2C shows cell viability at 1 day post electroporation as determined by trypan exclusion dye, (n=8 for all conditions). FIG. 2D shows a schematic of the donor integrase-defective lentiviral vector (IDLV): A 1.1 kb region of beta-globin was cloned in reverse with respect to the promoter elements in the long terminal repeat (LTRs) into a lentiviral backbone in which the 3' LTR contains the self-inactivating (SIN) deletion which is transferred during reverse transcription to the 5' LTR of the proviral DNA. UTR: untranslated region, RRE: rev-response element, Int: intron.

FIG. 3A shows gene modification rates at 3 days post electroporation as determined by qPCR for the RFLP. FIG. 3B shows fold expansion at 1 day post electroporation and FIG. 3C shows cell viability at 1 day post electroporation as determined by trypan exclusion dye, (n=6 for all conditions).

FIGS. 4A through 4F show correction using ZFN pair 33488/33501 at the beta-globin locus in CD34+ cells using an oligonucleotide donor. FIG. 4A shows a schematic of oligonucleotide-directed gene modification (SEQ ID NOs:4 and 5). FIG. 4B is a gel of an AvrII-digested PCR amplicon of the beta-globin locus. The fragment contains a native AvrII site, cleavage of which serves as an internal control for AvrII digestion (the lower band on the gel). Arrows indicate AvrII cleavage products. In the presence of the oligodonor and ZFN, there is a 15% gene correction rate. FIG. 4C shows six possible sites of silent mutation in the SBS#33501 ZFN binding site (SEQ ID NO:53 for WT and SEQ ID NO:54 for SMS). Sickle mutation italicized, possible silent mutation sites (SMS) in bold. FIG. 4D shows that silent mutations increased gene correction at beta-globin. mPB CD34+ cells were transfected with ZFNs and the indicated donor oligonucleotide. Introduction of the relevant silent mutation was assayed via high-throughput sequencing. White bars indicate insertions and deletions (indels); grey bars, gene correction. FIG. 4E shows that silent mutations block ZFN re-cleavage. Alleles with indels were examined for evidence of homology-mediated modification. Shown are the percentages of alleles with gene modification that also have evidence of NHEJ-driven indels. FIG. 4F shows optimization of ZFN concentration and donor type. NHEJ-drive indels (white bars) and gene correction (grey bars) were assayed by high-throughput DNA sequencing. Given the depth of high-throughput DNA sequencing, measurement error is expected to be very low. WT: wild-type; SMS: silent mutation sites; oligo: oligonucleotide.

FIGS. 6A and 6B depict partial HDR events and reveals that synthesis during oligo-mediated gene modification proceeds from left to right. FIG. 6A shows high-throughput DNA sequencing data from the ZFNs plus SMS124 donor from FIG. 3F that were assayed for evidence of partial HDR products (SMS1, SMS12, SMS24, and SMS4 alleles). Of the ~41% gene modification in this experiment, 6% of the modification came from SMS12 events whereas SMS24 alleles were almost completely absent (0.03%). This asymmetry implies that DNA synthesis proceeds from left to right. FIG. 6B demonstrates this using an average of data from all three ZFN concentrations are shown, with the events from the 30 and 60 µg/mL samples normalized upwards to match the ~41% gene modification seen in the 15 µg/mL sample.

FIGS. 7A through 7D show on-target cleavage analysis at beta-globin gene cluster. FIG. 7A is an illustration of GFP capture as follows: K562 erythroleukemia cells were electroporated with in vitro transcribed mRNA and transduced with an IDLV vector expressing GFP. Cells were cultured for 60 days to dilute out all non-trapped GFP after which GFP positive cells were sorted using fluorescence-activated cell sorting (FACS). nrLAM-PCR was performed on the samples and vector integration site analysis completed. An overview of the most common integration sites at beta-globin and delta-globin as determined using cluster analysis is shown. HBB: wild type human hemoglobin beta; HBD: human hemoglobin delta. FIG. 7B shows the alignment of partial globin gene sequences on chromosome 11 in the beta-globin gene cluster around the ZFN cut site (SEQ ID NOs:6 to 11). ZFN binding sites underlined, sickle mutation bold, italicized. HBB: wild type human hemoglobin beta; HBD: human hemoglobin delta; HBE1: human hemoglobin epsilon; HBBP1: human hemoglobin beta pseudogene 1; HBG1: human hemoglobin gamma A; HBG2: human hemoglobin gamma G. FIG. 7C is a gel showing a Surveyor® Nuclease assay of CD34+ cells treated with ZFN in vitro transcribed mRNA or untreated (Mock). Each of the indicated beta globin cluster genes was amplified surrounding the region of highest homology with the target site and cleaved with Surveyor® Nuclease. Bands were quantified by densitometry. FIG. 7D is a gel showing a Surveyor® Nuclease assay of SCD patient bone marrow samples as in FIG. 7B. Heterozygosity for a single nucleotide polymorphism in the gamma-globin gene produced background cleavage, even in the samples not exposed to ZFN (thin arrows).

FIG. 9A shows mPB CD34+ cells were transfected with ZFNs at 0, 3.75, 7.5, 15, or 30 µg/mL and an oligonucleotide donor at 3 µM or transfected with an oligonucleotide donor alone. Cells were induced to differentiate into red blood cells and aliquots removed after 0, 6, 12, 15, and 18 days. Genomic DNA was prepared from the cells and the frequency of gene-modified cells assayed via high-throughput sequencing. Approximately 10-50,000 sequence reads were obtained per sample per time point. FIG. 9B shows HPLC analysis of globin proteins in engineered cells.

FIGS. 10A through 10E show transplantation of ZFN and donor-treated cells into NSG mice. FIG. 10A shows gene modification rates of bulk transplanted cells treated with ZFN+IDLV and cultured in vitro as determined by qPCR for the RFLP at 7 days post electroporation. Mock cells are untreated, (n=3 independent experiments). FIG. 10B is a graph showing modification at the sickle base evaluated by high-throughput sequencing for ZFN+IDLV modified CD34+ cells. Results of sequencing of the beta-globin locus showing percentage of total aligned reads containing the changed wild-type to sickle base (T) as well as insertions and deletions (indels) at the cut site. Same samples as in FIG. 10A. Changed base, white; indels, gray. FIG. 10C is a graph showing the engraftment in the peripheral blood of transplanted mice at 5 weeks and 8 weeks post-transplant. Human engraftment determined as a percentage of hCD45+ cells out of the total hCD45+ and mCD45+ cells by flow cytometry of cells from mice receiving either mock- or ZFN+IDLV-treated cells. Mock, open diamonds; ZFN+IDLV, closed diamonds. (n=3 independent experiments; mock n=5, ZFN+IDLV n=12). FIG. 10D is a graph showing CD34+ cells were electroporated with Oligo, ZFN, or ZFN+Oligo and cultured in vitro before transplantation into NSG mice. Modification rates (n=1) at the sickle base and indels are shows as in FIG. 10C. FIG. 10E is a graph showing engraftment in the peripheral blood as in FIG. 10C, of cells from mice receiving either Oligo-, ZFN-, or ZFN+Oligo-treated cells. Oligo, circles; ZFN, triangles; ZFN+Oligo, diamonds. (Oligo n=8, ZFN n=7, ZFN+Oligo n=9), n.s.: not significant, *p<0.05, **p<0.01.

FIGS. 11A and 11B show lineage analysis of transplanted NSG mice at week 8. Immunophenotypic analysis of peripheral blood of NSG mice transplanted with mock and ZFN and donor treated cells at 8 weeks post-transplant. The percentage of the human CD45+ cells that were positive for the markers of B-cells (CD19), T-cells (CD3), hematopoietic progenitors (CD34), myeloid progenitors (CD33), and natural killer cells (CD56) was enumerated using flow cytometry. FIG. 11A is a graph showing the cells from mice transplanted with mock- or ZFN+IDLV-treated cells, (n=3 independent experiments; mock n=5, ZFN+IDLV n=12). FIG. 11B is a graph showing cells from mice transplanted with oligo-, ZFN-, or ZFN+Oligo-treated cells, (Oligo n=8, ZFN n=7, ZFN+Oligo n=9). n.s.: not significant; asterisk indicates significance, *p<0.05, **p<0.01.

FIG. 12A is a graph showing engraftment in the peripheral blood of transplanted mice at 16 weeks post-transplant. Human engraftment determined as a percentage of hCD45+ cells out of the total hCD45+ and mCD45+ cells by flow cytometry of cells from mice receiving either mock- or ZFN+IDLV-treated cells. Mock, open diamonds; ZFN+IDLV, closed diamonds. FIG. 12B is a graph showing immunophenotypic analysis of the peripheral blood of transplanted NSG mice at 16 weeks post-transplant. The percentage of the hCD45+ cells that were positive for the markers of B-cells (CD19), T-cells (CD3), hematopoietic progenitors (CD34), myeloid progenitors (CD33), and natural killer cells (CD56) was enumerated using flow cytometry of cells from mice receiving either mock- or ZFN+IDLV-treated cells. Mock, open diamonds; ZFN+IDLV, closed diamonds; (n=3 independent experiments; mock n=5, ZFN+IDLV n=12). FIG. 12C is a graph showing engraftment in the peripheral blood as in FIG. 12A of cells from mice receiving either Oligo-, ZFN-, or ZFN+Oligo-treated cells. Oligo, circles; ZFN, triangles; ZFN+Oligo, diamonds. FIG. 12D is a graph showing lineage analysis of the peripheral blood as in FIG. 12B of cells from mice receiving either Oligo-, ZFN-, or ZFN+Oligo-treated cells. Oligo, circles; ZFN, triangles; ZFN+Oligo, diamonds; (Oligo n=8, ZFN n=7, ZFN+Oligo n=9). n.s.: not significant, *p<0.05.

FIG. 13A is a graph showing gene modification rates in the bone marrow and spleen of transplanted mice at 16 weeks in cells from mice receiving either mock- or ZFN+IDLV-treated cells. Tissue was harvested, genomic DNA extracted and amplified, and qPCR for the incorporated RFLP analyzed. Mock, open diamonds; ZFN+IDLV, closed diamonds. FIG. 13B is a graph showing correction at the sickle mutation evaluated by high-throughput sequencing of samples described in FIG. 13A. Results of sequencing of the beta-globin locus showing percentage of total aligned reads containing the modified base at the sickle mutation. Mock, open diamonds; ZFN+IDLV, closed diamonds. (n=3 independent experiments; mock n=5, ZFN+IDLV n=12). FIG. 13C is a graph showing correction at the sickle mutation in cells from mice receiving either Oligo-, ZFN-, or ZFN+Oligo-treated cells as described in FIG. 13B. Oligo, circles; ZFN, triangles; ZFN+Oligo, diamonds. (Oligo n=8, ZFN n=7, ZFN+Oligo n=9). n.s.: not significant; asterisk indicates significance, *p<0.05, **p<0.01.

FIG. 14A is a graph showing engraftment in the bone marrow of transplanted mice at 16 weeks post-transplant. Human engraftment determined as a percentage of hCD45+ cells out of the total hCD45+ and mCD45+ cells by flow cytometry of cells from mice receiving either mock- or ZFN+IDLV-treated cells. Mock, open diamonds; ZFN+IDLV, closed diamonds. FIG. 14B is a graph showing immunophenotypic analysis of bone marrow of transplanted NSG mice at 16 weeks post-transplant. The percentage of the hCD45+ cells that were positive for the markers of B-cells (CD19), T-cells (CD3), hematopoietic progenitors (CD34), myeloid progenitors (CD33), and natural killer cells (CD56) was enumerated using flow cytometry of cells from mice receiving either mock- or ZFN+IDLV-treated cells. Mock, open diamonds; ZFN+IDLV, closed diamonds; (n=3 independent experiments; mock n=5, ZFN+IDLV n=12). FIG. 14C is a graph showing engraftment in the bone marrow as in FIG. 14A of cells from mice receiving either Oligo-, ZFN-, or ZFN+Oligo-treated cells. Oligo, circles; ZFN, triangles; ZFN+Oligo, diamonds. FIG. 14D is a graph showing lineage analysis of the bone marrow as in FIG. 14B of cells from mice receiving either Oligo-, ZFN-, or ZFN+Oligo-treated cells. Oligo, circles; ZFN, triangles; ZFN+Oligo, diamonds; (Oligo n=8, ZFN n=7, ZFN+Oligo n=9). n.s.: not significant, *p<0.05.

FIG. 15A is a graph showing the fold expansion of SCD patient bone marrow CD34+ cells that were electroporated with in vitro transcribed ZFN mRNA and transduced with donor IDLV carrying the WT base at the sickle location and grown under erythroid conditions. FIG. 15B is a graph of total colony forming units for each type of hematopoietic colony identified per 200 cells plated are represented. FIG. 15C is a graph showing the percentage of colonies formed relative to total number of cells plated. CFU: colony-forming unit; BFU: blast-forming unit; GEMM: granulocyte, erythrocyte, monocyte, and macrophage; E: erythroid, GM: granulocyte and macrophage; G: granulocyte; M: monocyte, asterisk indicates significance, *p<0.05, **p<0.01, (n=2 independent experiments; Mock n=3; ZFN Only n=4; IDLV Only n=3, ZFN+IDLV n=6).

FIGS. 16A through 16D show functional correction of sickle bone marrow CD34+ cells. Sickle cell disease patient bone marrow CD34+ cells were electroporated with in vitro transcribed ZFN mRNA and transduced with donor IDLV carrying the WT base at the sickle location and grown under erythroid conditions. FIG. 16A is a graph showing gene modification rates analyzed by qPCR for the incorporated RFLP at 12 days post electroporation. FIG. 16B is a graph showing correction at the sickle mutation evaluated by high-throughput sequencing. Results of sequencing of the beta-globin locus showing percentage of total aligned reads containing the corrected WT base (A) at the sickle mutation as well as insertions and deletions (indels) at the cut site. Corrected base, white; indels, gray. FIG. 16C shows HPLC analysis of differentiated erythroid cells at the termination of culture. Cells were pelleted, lysed, and supernatant was analyzed by high performance liquid chromatography (HPLC). The left panel shows a SCD mock sample and the right panel shows a SCD ZFN+IDLV sample. Shading indicates HbA: WT adult hemoglobin peak. FIG. 16D is a graph of the quantification of the percent of HbA out of the total area under the curve represented by the main peaks. HbA: WT adult hemoglobin, HbF: Fetal hemoglobin, HbS: sickle hemoglobin. n.s.: not significant, (n=2 independent experiments; Mock n=3; ZFN Only n=4; IDLV Only n=3, ZFN+IDLV n=6).

FIG. 17A shows the frequency of NHEJ DNA repair. FIG. 17B shows the frequency of homology-dependent DNA repair. In addition to the sickle-cell mutation, the oligonucleotide donor includes either the SMS12 mutations (black bars) or the SMS012 mutations (grey bars) shown in FIG. 4C.

DETAILED DESCRIPTION

Figure 1C:
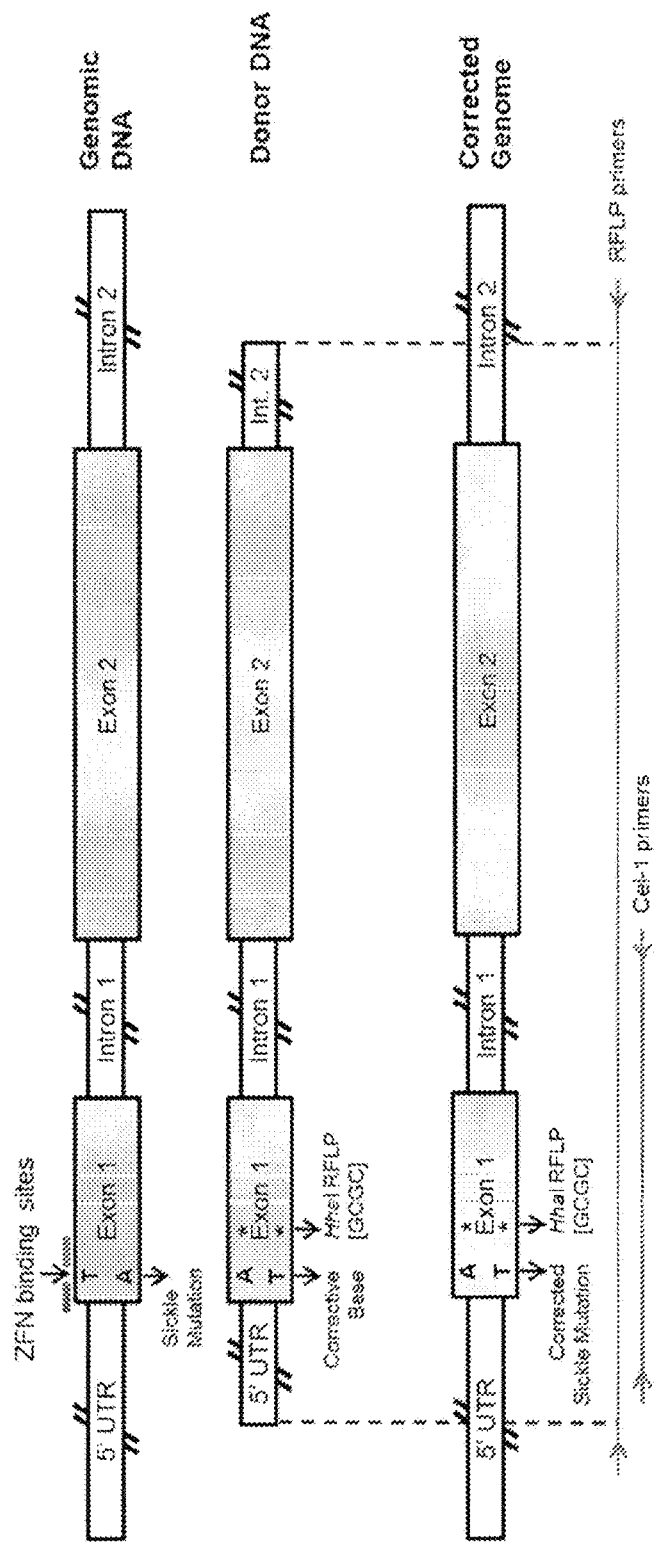

Disclosed herein are compositions and methods for transduction of a cell for use in gene therapy or genome engineering. In particular, nuclease-mediated (i.e. ZFN, TALEN, TtAgo or CRISPR/Cas system) targeted integration of an exogenous sequence or genome alteration by targeted cleavage is efficiently achieved in a cell. Particularly useful for transduction and engineering of HSC/PC, the methods and compositions can also be used for other cell types to provide genetically modified cells comprising insertions and/or deletions in a globin gene. Specifically, the methods and compositions of the invention are useful for editing a globin gene by correcting a disease associated allele for the treatment and prevention of sickle cell disease.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, Sari Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant (IQ) of $10^{-6}$ $M^{-1}$ or lower. "Affinity" refers to the strength of binding: increased binding affinity being correlated with a lower IQ.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; 6,534,261 and 8,586,526; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 8,586,526; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g. Swarts et al, ibid, G. Sheng et al., (2014) *Proc. Natl. Acad. Sci. U.S.A.* 111, 652). A "TtAgo system" is all the components required including e.g. guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break (DSB) in the target sequence (e.g., cellular chromatin) at a predetermined site. The DSB may result in deletions and/or insertions by homology-directed repair or by non-homology-directed repair mechanisms. Deletions may include any number of base pairs. Similarly, insertions may include any number of base pairs including, for example, integration of a "donor" polynucleotide, optionally having homology to the nucleotide sequence in the region of the break. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins, TALENs, TtAgo and/or CRIPSR/Cas systems can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Pat. Nos. 7,888,121; 7,914,796; 8,034,598 and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid Call be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster. Methods for the introduction of exogenous molecules into plant cells are known to those of skill in the art and include, but are not limited to, protoplast transformation, silicon carbide (e.g., WHISKERS™), Agrobacterium-mediated transformation, lipid-mediated transfer (i.e., liposomes, including neutral and cationic lipids), electroporation, direct injection, cell fusion, particle bombardment (e.g., using a "gene gun"), calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP, TALE, TtAgo or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells), including stem cells (pluripotent and multipotent).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE, TtAgo or Cas DNA-binding domain is fused to an activation domain, the ZFP, TALE, TtAgo or Cas DNA-binding domain and the activation domain are in operative linkage if, in the fusion polypeptide, the ZFP, TALE, TtAgo or Cas DNA-binding domain portion is able to bind its target site and/or its binding site, while the activation domain is able to upregulate gene expression. When a fusion polypeptide in which a ZFP, TALE, TtAgo or Cas DNA-binding domain is fused to a cleavage domain, the ZFP, TALE, TtAgo or Cas DNA-binding domain and the cleavage domain are in operative linkage if, in the fusion polypeptide, the ZFP, TALE, TtAgo or Cas DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the nucleases, donors and/or genetically modified cells of the invention can be administered. Subjects of the present invention include those with a disorder.

"Stemness" refers to the relative ability of any cell to act in a stem cell-like manner, i.e., the degree of toti-, pluri-, or oligo-potency and expanded or indefinite self-renewal that any particular stem cell may have.

Factors that Enhance Stem Cell Expansion

Any factor or factors that enhance stem cell expansion and/or differentiation can be used in the practice of the present invention. The factors may be introduced directly into the cell (for example, as genes encoding the factor(s)) and/or may be introduced into the surrounding culture medium (including feeder layers and other solid substrates) to affect the cells. The use of such factors, for example in the culture conditions before, during or after nuclease-mediated modification is induced, increases the rate of nuclease-mediated modification of the stem cell.

Non-limiting examples of factors that can be used include SR1, an aryl hydrocarbon receptor antagonist, dmPGE2, a prostaglandin, UM171 and UM729, compounds identified in a library screen (see Pabst et al (2014) Nat Meth 11:436-442), rapamycin (see Wang et al (2014) Blood. pii: blood-2013-12-546218), angiopoietin-like proteins ("Angptls", e.g. Notch/delta/ANGPTL5 (see Zhang et al (2008) Blood. 111(7):3415-3423), Angptl2, Angptl3, Angptl5, Angptl7, and Mfap4), the copper chelator tetraethyletepentamine (TEPA, see de Lima et al (2008) Bone Mar Trans 41:771-778), histone deacetylase (HPAC) inhibitors, e.g. valproic acid (see Chaurasia et al (2014) J Clin Invest 124:2378-2395), IGF-binding protein 2 (IGFBP2), nicotinamide (see Horwitz et al (2014) J. Clin. Invest 124:3121-3128), Tat-myc (see WO2010025421) and tat-Bcl2 (see WO2014015312) fusion proteins, MAPK14/p38a Ly2228820 (see Baudet et al (2012) Blood 119(26):6255-6258), products of self-renewing genes such as HOXB4, OCT3/4 cord blood and/or MSC derived feeder layers or an ex vivo vascular niche co-culture system termed E4+EC (see Butler et al (2012) Blood. 120(6): 1344-1347), cytokines, (by way of non-limiting example Stemspan™ CC110, CC100, and/or H3000 (Stemcell™ technologies), Flt-3 ligand, SCF, TPO)

In some embodiments, the factors comprise StemRegenin (SR1, see, e.g., U.S. Pat. No. 8,741,640; Boitano et al, (2010) *Science* 329(5997):1345-1348), an aryl hydrocarbon receptor (AhR) antagonist that promotes expansion of CD34+ cells ex vivo is used in the methods and compositions described herein. In other embodiments, the factors comprise UM171 (see Fares et al (2013) *Blood:* 122 (21)), which is an agonist of stem cell renewal. In still other aspects, the factor comprises one or more prostaglandins, for example, dmPGE2. See, e.g., U.S. Pat. No. 8,168,428; North et al (2007) *Nature* 447(7147): 1007-1011). In some aspects, the factor comprises one or more hormones such as angiopoietin-like proteins ("Angptls", e.g. Angptl2, Angptl3, An t15, Angptl7, and Mfap4) and IGF-binding protein 2 (IGFBP2) are used. See, e.g., U.S. Pat. No. 7,807,464; Zhang et al (2008) 111(7): 3415-3423). In other aspects, the factors comprise one or more protein products of self-renewing genes such as HOXB4 or OCT are used. See, e.g., U.S. Pat. No. 8,735,153; Watts et al (2012) *Exp Hematol.* 40(3): 187-196). Alternatively these genes may be transiently expressed in the culture medium and/or in the stem cells.

The factors that affect stem cell expansion may be also comprise cellular support methods, including but not limited to feeder layers derived from stromal cell and/or MSC derived cells. See, e.g., Breems et al (1998) *Blood* 91(1): 111-117 and Magin et al., (2009) *Stem Cells Dev.* 2009 January-February; 18(1):173-86.

Any suitable amount of one or more factors that enhance stem cell expansion may be used, so long as it is effective to increase nuclease activity and nuclease-mediated genomic modification. The particular concentrations used can be readily determined by one of skill in the art. In certain embodiments, between 0.1 nM and 100 µM is used, for example between 0.5 µM to 25 µM concentrations is used, including any amount therebetween (e.g., 1 µM to 20 µM, 3 µM to 10 µM, etc.).

Fusion Molecules

Described herein are compositions, for example nucleases, that are useful for cleavage of a selected target gene in a cell, particularly a stem cell. In certain embodiments, one or more components of the fusion molecules (e.g., nucleases) are naturally occurring. In other embodiments, one or more of the components of the fusion molecules (e.g., nucleases) are non-naturally occurring, i.e., engineered in the DNA-binding domain(s) and/or cleavage domain(s). For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains).

A. DNA-Binding Molecules

In certain embodiments, the composition and methods described herein employ a meganuclease (homing endonuclease) DNA-binding molecule (also referred to as a DNA-binding domain) for binding to the donor molecule and/or binding to the region of interest in the genome of the cell. Naturally-occurring meganucleases recognize 15-40 base-pair cleavage sites and are commonly grouped into four families: the LAGLIDADG family ("LAGLIDADG" disclosed as SEQ ID NO: 71), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases iii important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet.* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 base pairs in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 base pairs and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVD) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN). See, e.g., U.S. Pat. No. 8,586,526; Christian et al ((2010)<*Genetics* epub 10.1534/genetics.110.120717). In certain embodiments, TALE domain comprises an N-cap and/or C-cap as described in U.S. Pat. No. 8,586,526.

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Selection of target sites and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system, including, for example a single guide RNA (sgRNA). See, e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. *Mol. Microbiol.* 43:1565-1575; Makarova et al., 2002. *Nucleic Acids Res.* 30:482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olovnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. Ago-RNA-mediated DNA cleavage could be used to affect a panopoly of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity, including for use in genome modification in a variety of organisms. See, for example, United States Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586,526. CRISPR/Cas nuclease systems comprising single guide RNAs (sgRNAs) that bind to DNA and associate with cleavage domains (e.g., Cas domains) to induce targeted cleavage have also been described. See, e.g., U.S. Pat. Nos. 8,697,359 and 8,932,814 and U.S. Patent Publication No. 20150056705.

As noted above, the cleavage domain may be heterologous to the DNA-binding domain, for example: a zinc finger DNA-binding domain and a cleavage domain from a nuclease; a TALEN DNA-binding domain and a cleavage domain from a nuclease; a sgRNA DNA-binding domain and a cleavage domain from a nuclease (CRISPR/Cas); and/or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. Additional enzymes which cleave DNA are known (e.g., Si Nuclease; mung bean nuclease; pancreatic DNase I; micrococcal nuclease; yeast HO endonuclease. One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci.* USA 89:4275-4279; Li et al. (1993) *Proc. Natl. Acad. Sci.* USA 90:2764-2768; Kim et al. (1994a) *Proc. Natl. Acad. Sci.* USA 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci.* USA 95:10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20090305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Cleavage domains with more than one mutation may be used, for example mutations at positions 490 (E→K) and 538 (I→K) in one cleavage half-domain to produce an engineered cleavage half-domain designated "E490K: I538K" and by mutating positions 486 (Q→E) and 499 (I→L) in another cleavage half-domain to produce an engineered cleavage half-domain designated "Q486E:I499L;" mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively); engineered cleavage half-domain comprising mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively); and/or engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. Nos. 7,914,796; 8,034,598 and 8,623,618, the disclosures of which are incorporated by reference in its entirety for all purposes. In other embodiments, the engineered cleavage half domain comprises the "Sharkey" and/or "Sharkey'" mutations (see Guo et al, (2010) *J. Mol. Biol.* 400(1):96-107).

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek et al., (2012) Science 337: 816-821, Jinek et al., (2013) eLife 2:e00471. DOI: 10.7554/eLife.00471 and Cong, ibid).

Target Sites

As described in detail above, DNA-binding domains can be engineered to bind to any sequence of choice. An engineered DNA-binding domain can have a novel binding specificity, compared to a naturally-occurring DNA-binding domain.

Non-limiting examples of suitable target genes a beta (β) globin gene (HBB), a gamma (δ) globin gene (HBG1), a B-cell lymphoma/leukemia 11A (BCL11A) gene, a Kruppel-like factor 1 (KLF1) gene, a CCR5 gene, a CXCR4 gene, a PPP1R12C (AAVS1) gene, an hypoxanthine phosphoribosyltransferase (HPRT) gene, an albumin gene, a Factor VIII gene, a Factor IX gene, a Leucine-rich repeat kinase 2 (LRRK2) gene, a Huntingtin (Htt) gene, a rhodopsin (RHO) gene, a Cystic Fibrosis Transmembrane Conductance Regulator (CFTR) gene, a surfactant protein B gene (SFTPB), a T-cell receptor alpha (TRAC) gene, a T-cell receptor beta (TRBC) gene, a programmed cell death 1 (PD1) gene, a Cytotoxic T-Lymphocyte Antigen 4 (CTLA-4) gene, an human leukocyte antigen (HLA) A gene, an HLA B gene, an HLA C gene, an HLA-DPA gene, an HLA-DQ gene, an HLA-DRA gene, a LMP7 gene, a Transporter associated with Antigen Processing (TAP) 1 gene, a TAP2 gene, a tapasin gene (TAPBP), a class II major histocompatibility complex transactivator (CIITA) gene, a dystrophin gene (DMD), a glucocorticoid receptor gene (GR), an IL2RG gene, a Rag-1 gene, an RFX5 gene, a FAD2 gene, a FAD3 gene, a ZP15 gene, a KASII gene, a MDH gene, and/or an EPSPS gene.

In certain embodiments, the nuclease targets a "safe harbor" loci such as the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Donors

In certain embodiments, the present disclosure relates to nuclease-mediated modification of the genome of a stem cell. As noted above, insertion of an exogenous sequence (also called a "donor sequence" or "donor" or "transgene"), for example for deletion of a specified region and/or correction of a mutant gene or for increased expression of a wild-type gene. It will be readily apparent that the donor sequence is typically not identical to the genomic sequence where it is placed. A donor sequence can contain a non-homologous sequence flanked by two regions of homology to allow for efficient HDR at the location of interest or can be integrated via non-homology directed repair mechanisms. Additionally, donor sequences can comprise a vector molecule containing sequences that are not homologous to the region of interest in cellular chromatin. A donor molecule can contain several, discontinuous regions of homology to cellular chromatin. Further, for targeted insertion of sequences not normally present in a region of interest, said sequences can be present in a donor nucleic acid molecule and flanked by regions of homology to sequence in the region of interest.

As with nucleases, the donors can be introduced into any form. In certain embodiments, the donors are introduced in mRNA form to eliminate residual virus in the modified cells. In other embodiments, the donors may be introduced using DNA and/or viral vectors by methods known in the art. See, e.g., U.S. Patent Publication Nos. 20100047805 and 20110207221. The donor may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci.* USA 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

In certain embodiments, the donor includes sequences (e.g., coding sequences, also referred to as transgenes) greater than 1 kb in length, for example between 2 and 200 kb, between 2 and 10 kb (or any value therebetween). The donor may also include at least one nuclease target site. In certain embodiments, the donor includes at least 2 target sites, for example for a pair of ZFNs, TALENs, TtAgo or CRISPR/Cas nucleases. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor can be inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter. The donor molecule may be inserted into an endogenous gene such that all, some or none of the endogenous gene is expressed. Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In some embodiments, the donor further comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

In certain embodiments, the transgene may include, for example, wild-type genes to replace mutated endogenous sequences. For example, a wild-type (or other functional) gene sequence may be inserted into the genome of a stem cell in which the endogenous copy of the gene is mutated. The transgene may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes). Exemplary splice acceptor site sequences are known to those of skill in the art and include, by way of example only, CTGACCTCTTCTCT-TCCTCCCACAG, (SEQ ID NO:1) (from the human HBB gene) and TTTCTCTCCACAG (SEQ ID NO:2) (from the human Immunoglobulin-gamma gene).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Cells

Thus, provided herein are genetically modified cells, for example stem cells comprising an inactivated gene and/or a transgene, including cells produced by the methods described herein. The transgene is integrated in a targeted manner into the cell's genome using one or more nucleases. Unlike random integration, targeted integration ensures that the transgene is integrated into a specified gene. The transgene may be integrated anywhere in the target gene. In certain embodiments, the transgene is integrated at or near the nuclease binding and/or cleavage site, for example, within 1-300 (or any number of base pairs therebetween) base pairs upstream or downstream of the site of cleavage and/or binding site, more preferably within 1-100 base pairs (or any number of base pairs therebetween) of either side of the cleavage and/or binding site, even more preferably within 1 to 50 base pairs (or any number of base pairs therebetween) of either side of the cleavage and/or binding site. In certain embodiments, the integrated sequence does not include any vector sequences (e.g., viral vector sequences). In certain embodiments, the cells comprise a modification (e.g., insertion and/or deletion) made by a nuclease as described herein such that the modification is within an exon of the beta-globin gene, for example within exon 1, 2 or 3. In certain embodiments, the modification corrects a sickle-cell mutation in exon 1 of the beta globin gene. In certain embodiments, the modification is at or near (e.g., 1-300 base pairs or any number of base pairs therebetween) SEQ ID NO:23 or 24. In other embodiments, the modification is 1-100 (or any number of base pairs therebetween) base pairs of SEQ ID NO:23 or 24. In certain embodiments, the modification is within SEQ ID NO:23 and/or SEQ ID NO:24, for example a modification of 1 or more base pairs in either SEQ ID NO:23 or 24.

Any cell type can be genetically modified as described herein to comprise a transgene, including but not limited to cells and cell lines. Other non-limiting examples of genetically modified cells as described herein include T-cells (e.g., CD4+, CD3+, CD8+, etc.); dendritic cells; B-cells; autologous (e.g., patient-derived). In certain embodiments, the cells are stem cells, including heterologous pluripotent, totipotent or multipotent stem cells (e.g., CD34+ cells, induced pluripotent stem cells (iPSCs), embryonic stem cells or the like). In certain embodiments, the cells as described herein are stem cells derived from patient.

The cells as described herein are useful in treating and/or preventing disorders in a subject with the disorder, for example, by ex vivo therapies. The nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional protein (from the inserted donor) also occurs. Pharmaceutical compositions comprising the cells as described herein are also provided. In addition, the cells may be cryopreserved prior to administration to a patient.

Delivery

The nucleases, polynucleotides encoding these nucleases, donor polynucleotides and compositions comprising the proteins and/or polynucleotides described herein may be delivered by any suitable means. In certain embodiments, the nucleases and/or donors are delivered in vivo. In other embodiments, the nucleases and/or donors are delivered to isolated cells (e.g., autologous or heterologous stem cells) for the provision of modified cells useful in ex vivo delivery to patients.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using any nucleic acid delivery mechanism, including naked DNA and/or RNA (e.g., mRNA) and vectors containing sequences encoding one or more of the components. Any vector systems may be used including, but not limited to, plasmid vectors, DNA minicircles, retroviral vectors, lentiviral vectors, adenovirus vectors, poxvirus vectors; herpesvirus vectors and adeno-associated virus vectors, etc., and combinations thereof. See, also, U.S. Pat. Nos. 6,534,261; 6,607,882; 6,824,978; 6,933, 113; 6,979,539; 7,013,219; and 7,163,824, and U.S. patent application Ser. No. 14/271,008, incorporated by reference herein in their entireties. Furthermore, it will be apparent that any of these systems may comprise one or more of the sequences needed for treatment. Thus, when one or more nucleases and a donor construct are introduced into the cell, the nucleases and/or donor polynucleotide may be carried on the same delivery system or on different delivery mechanisms. When, multiple systems are used, each delivery mechanism may comprise a sequence encoding one or multiple nucleases and/or donor constructs (e.g., mRNA encoding one or more nucleases and/or mRNA or AAV carrying one or more donor constructs).

Conventional viral and non-viral based gene transfer methods can be used to introduce nucleic acids encoding nucleases and donor constructs in cells (e.g., mammalian cells) and target tissues. Non-viral vector delivery systems include DNA plasmids, DNA minicircles, naked nucleic acid, and nucleic acid complexed with a delivery vehicle such as a liposome, lipid nanoparticle, poly-lactate-glycolic acid nanoparticles, poly-amine complexing agents, or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11; 162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, naked RNA, capped RNA, artificial virions, and agent-enhanced uptake of DNA. Sonoporation using, e.g., the Sonitron 2000 system (RichMar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™) Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered CRISPR/Cas systems take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of CRISPR/Cas systems include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989). Any AAV serotype can be used, including AAV1, AAV3, AAV4, AAV5, AAV6 and AAV8, AAV 8.2, AAV9, and AAV rh10 and pseudotyped AAV such as AAV2/8, AAV2/5 and AAV2/6.

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 base pair (bp) inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9 and AAVrh10, and all variants thereof, can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Naldini et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/0054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by an or AAV, while the one or more nucleases can be carried by mRNA. Furthermore, the different systems can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Kits

Also provided are kits for performing any of the above methods. The kits typically contain polynucleotides encoding one or more nucleases, one or more factors that affect stem cell expansion and/or donor polynucleotides as described herein as well as instructions for administering the factors that affect stem cells into the cells into which the nucleases and/or donor polynucleotide are introduced (or surrounding media). The kits can also contain cells, buffers for transformation of cells, culture media for cells, and/or buffers for performing assays. Typically, the kits also contain a label which includes any material such as instructions, packaging or advertising leaflet that is attached to or otherwise accompanies the other components of the kit.

The following Examples relate to exemplary embodiments of the present disclosure in which the nuclease comprises one or more ZFNs or one or more TALENs. It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases) DNA-binding domains and heterologous cleavage domains, mega TALs, compact TALENs and nuclease systems such as TtAgo and CRISPR/Cas using engineered single guide RNAs.

EXAMPLES

Example 1: Design, Construction and General Characterization of Zinc Finger Protein Nucleases (ZFN)

Zinc finger proteins were designed and incorporated into plasmids, AAV or adenoviral vectors essentially as described in Urnov et al. (2005) *Nature* 435(7042):646-651, Perez et al (2008) *Nature Biotechnology* 26(7):808-816, and as described in U.S. Pat. No. 6,534,261 and tested for binding. For ZFNs and TALENs specific for the human beta globin locus, see co-owned U.S. Pat. No. 7,888,121 and U.S. Patent Publication Nos. 20130137104 and 20130122591.

Example 2: Activity of Globin-Specific ZFNs

ZFN pairs targeting the human globin locus were used to test the ability of these ZFNs to induce DSBs at a specific target site. The amino acid sequences of the recognition helix regions of each finger of the indicated ZFNs are shown below in Table 1. The target sites (DNA target sites indicated in uppercase letters; non-contacted nucleotides indicated in lowercase) are shown in Table 2.

TABLE 1

Human beta globin-specific zinc finger proteins recognition helix designs

| SBS # | F1 | F2 | F3 | F4 | F5 | F6 |
|---|---|---|---|---|---|---|
| 33488 | LRHHLTR (SEQ ID NO: 12) | LRHNLRA (SEQ ID NO: 13) | DQSNLRA (SEQ ID NO: 14) | RNASRTR (SEQ ID NO: 15) | RSDNLSE (SEQ ID NO: 16) | RSQHRKT (SEQ ID NO: 17) |
| 33501 | TSGSLSR (SEQ ID NO: 18) | DRSDLSR (SEQ ID NO: 19) | DRSALAR (SEQ ID NO: 20) | QSSNLAR (SEQ ID NO: 21) | QSGHLSR (SEQ ID NO: 22) | NA |
| 47773 | LRHHLTR (SEQ ID NO: 12) | LKQNLDA (SEQ ID NO: 55) | DQSNLRA (SEQ ID NO: 14) | RNCARLR (SEQ ID NO: 56) | RSDNLSE (SEQ ID NO: 16) | RNQTRLN (SEQ ID NO: 57) |
| 47817 | HHHSLKR (SEQ ID NO: 58) | DRSDLSR (SEQ ID NO: 19) | TNSELDR (SEQ ID NO: 59) | QSSNLAR (SEQ ID NO: 21) | QSGHLSR (SEQ ID NO: 22) | NA |

TABLE 2

Target Sites of human beta globin-specific zinc fingers

| SBS # | Target site |
|---|---|
| 33488, 47773 | ggAGTCAGGTGCACCATGGTgtctgttt (SEQ ID NO: 23) |
| 33501, 47817 | gtGGAGAAGTCtGCCGTTactgccctgt (SEQ ID NO: 24) |

Human CD34+ cells were obtained and processed as follows. All cord blood (CB) specimens were obtained according to guidelines approved by the University of California, and deemed anonymous medical waste exempt from IRB review. Cells were processed within 48 hours of collection. Bone marrow (BM) aspirates from volunteer donors with SCD were obtained with informed consent under UCLA IRB protocol #10-001399. Mononuclear cells (MNC) were isolated from BM and CB using Ficoll Hypaque (Stem Cell Technologies) density centrifugation. Immunomagnetic column separation was then used to enrich for CD34+ cells by incubating the MNCs with anti-CD34 microbeads (Miltenyi Biotec Inc.) at 4° C. for 30 min. Cells were then sent through the magnetic column and CD34+ cells collected and placed in cryovials with freezing medium (10% Dimethyl sulfoxide (Sigma Aldrich), 90% FBS) and cryopreserved in liquid nitrogen. Mobilized CD34+ cells (mPB) were purchased from Allcells.

To produce the mRNA for electroporation, plasmids encoding the ZFNs shown in Table 1 were linearized with SpeI (New England Biolabs) and purified by phenol:cholorform before use as a template for in vitro transcription. The mMessage mMachine® T7 ULTRA Transcription kit (Life Technologies) was used according to the manufacturer's protocol to produce in vitro transcribed mRNA and cleaned up with the RNeasy® MinElute® Cleanup Kit (Qiagen). For electroporation, the following protocol was followed: CB CD34+ cells were thawed at 37° C., washed in Iscove's Modified Dulbecco's Medium (IMDM; Life Technologies) supplemented with 20% Fetal Bovine Serum (Gemini Bio-products) and (1× glutamine, penicillin, and streptomycin) and pre-stimulated for 48 hours in X-VIVO15 media (Lonza) containing glutamine, penicillin, streptomycin, 50 ng/ml SCF, 50 ng/ml Flt-3 and 50 ng/ml TPO (Peprotech). For electroporation, 200,000 cells per reaction were spun at 90 g for 15 min, resuspended in 100 µl of BTX press buffer (Harvard Apparatus), mixed with indicated amounts of ZFN mRNA and/or oligonucleotide as applicable, and pulsed once at 250V for 5 msec in the BTX ECM 830 Square Wave Electroporator (Harvard Apparatus).

Following electroporation, cells rested for 10 minutes at room temperature before the addition of culture media and transfer to plates in a total of 500 ul. The donor IDLV was present in the final culture medium at the concentrations described for appropriate samples.

Gene correction and gene disruption were analyzed as follows: Surveyor® Nuclease Assay (Cel-1) was used to determine ZFN induced site-specific allelic disruption. A 410 bp region surrounding the ZFN binding site was PCR amplified from 200 ng of genomic DNA using CellFwd (5'-gacaggtacggctgtcatca-3' SEQ ID NO:25) and CellRev (5'-cagcctaagggtgggaaaat-3' SEQ ID NO:26) using Accuprime Taq Hi-Fi (Life Technologies). Denaturation, reannealing, digestion, and electrophoretic and densitometry analysis were completed as described (e.g. Joglekat et al (2013) *Mol. Ther: J of the Amer Soc Gene Ther* 21: 1705-17). Site-specific gene modification was detected by Restriction Fragment Length Polymorphism (RFLP).

A 1.1 kb region surrounding the ZFN binding site was PCR amplified using primers BgloOuterFwd (5'-atgctta-gaaccgaggtagagttt-3', SEQ ID NO:27) and BgloOuterRev (5'-cctgagacttccacactgatg-3', SEQ ID NO:28) and Accuprime Taq Hi-Fi (Life Technologies). The PCR product was purified using PCR cleanup kit (Life Technologies) and digested using 10 units of HhaI (New England Biolabs) for 3.5 hours at 37° C. The digestion products were separated on 1.0% TBE-Agarose gel pre-stained with GelGreen (Biotium) and imaged on a Typhoon FLA 9000 Biomolecular Imager (GE Healthcare).

To quantify gene modification, a quantitative PCR based assay was used. A set of two PCR reactions were performed using the 1.1 kb PCR product described above as a template. The unpurified PCR template was diluted 1:5,000 of which 1 ul was used in each of the following 25 ul reactions. The first PCR was performed to amplify modified genomes, using primers HhaIFwd (5'-gaagtctgccgttactgcg-3', SEQ ID NO:29) and HhaIRev (5'-cccagtttctattggtctcc-3', SEQ ID NO:30). The second PCR was performed to normalize the input template using primers ExonIIFwd (5'-ctcggtgcctttagt-gatgg-3', SEQ ID NO:31) and ExonIIRev (5'-gactcaccct-gaagttctc-3', SEQ ID NO:32). Both of these PCRs were made quantitative using Power SYBR Green PCR Master Mix (Life Technologies) and acquired on ViiA7 (Life Technologies). Frequency of gene modification was determined using the Ct (cycles to threshold) difference between the two reactions and a plasmid standard curve. All ZFNs were found to be active.

Globin paralogs were PCR-amplified and deep-sequenced on an Illumina MiSeq machine to assay off target modification. The primers used for PCR are as follows: HBB: 5'-acacgacgctcttccgatctnnnngggctgggcataaaagtcag-3' (SEQ ID NO:33) and 5'-gacgtgtgctcttccgatcttccacatgcccagtttctatt-3' (SEQ ID NO:34); HBD: 5'-acacgacgctcttc-cgatctnnnntaaaaggcagggcagagtcga-3' (SEQ ID NO:35) and 5'-gacgtgtgctcttccgatctacatgcccagtttccatttgc-3' (SEQ ID NO:36); HBE1: 5'-acacgacgctc ttccgatctnnnnnctgcttccga-cacagctgcaa-3' (SEQ ID NO:37) and 5'-gacgtgtgctcttccgatct-tcacccttcattcccatgcat-3' (SEQ ID NO:38); HBG1 and HBG2: 5'-acacgacgctcttccgatctnnnnggaacgtctgaggttatcaat-3' (SEQ ID NO.39) and 5'-gacgtgtgctcttccgatcttccttccctcccttgtcc-3' (SEQ ID NO:40). HBG1 and HBG2 were co-amplified and sequence reads were assigned to either HBG1 or HBG2 using locus-specific SNPs within the amplicon. Mixed bases within the forward primers allow for cluster deconvolution during sequencing.

The ZFNs induced 35-65% allelic disruption (indels) at the beta-globin locus depending on the cell type, while detected modification at the beta globin paralogs was lower, as shown below in Table 3.

TABLE 3

ZFN-associated modification at human beta globin and its paralogs in K562 or CD34+ cells (33488/33501)

| | NHEJ detected by Illumina sequencing (%) | |
|---|---|---|
| Gene | K562 cells | Human CD34+ cells |
| HBB | 66.600 | 37.500 |
| HBD | 34.000 | 28.600 |
| HBE1 | 0.000 | 0.000 |
| HBG1 | 0.006 | 0.000 |
| HBG2 | 0.013 | 0.005 |
| HBBP1 | 0.024 | 0.005 |

Electroporation of in vitro transcribed mRNA encoding the ZFNs into CD34+ isolated from both human umbilical cord blood (CB) as well as mobilized peripheral blood (mPB) resulted in effective cleavage of the target locus, as determined by the Surveyor Nuclease assay (FIG. 1B).

The results showed that ZFNs drive high levels of gene modification at the beta-globin locus.

Example 4: ZFN Driven Correction at the Sickle Cell Base

Figure 2A:
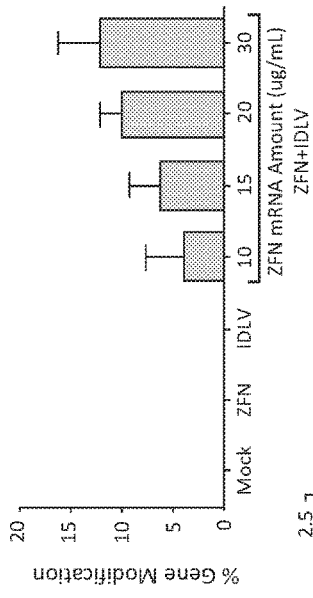
FIGS. 2A through 2D show results of optimization the ZFN and IDLV doses used for transduction.
Figure 2B:
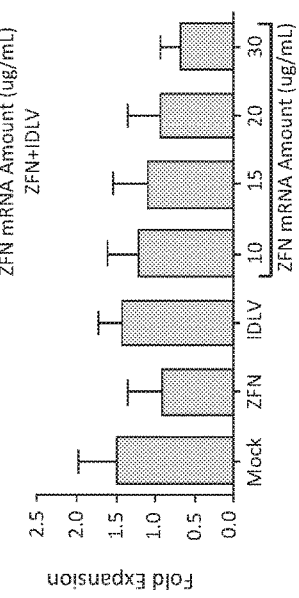
Figure 2C:
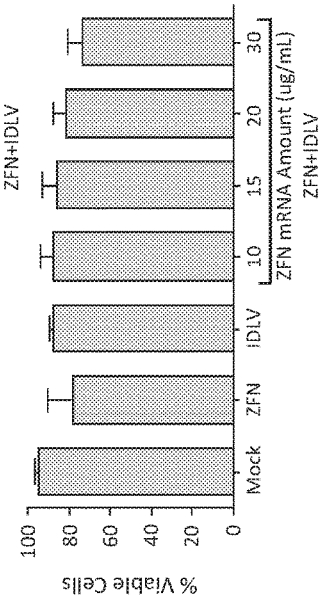
Figure 2D:
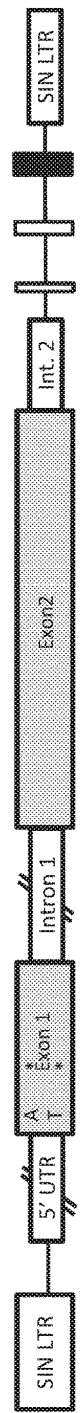

Following successful cleavage at the targeted beta-globin locus, we sought to determine if correction of the sickle base at this site was possible using a homologous donor template. To this end, two types of gene correction templates were designed and tested in parallel: a short DNA oligo and an IDLV. The 1.1 kb human beta-globin gene fragment donor template cloned into the IDLV was designed to include the corrective change at the sickle mutation, as well as a silent restriction fragment length polymorphism (RFLP) to create a HhaI restriction site for surrogate analysis of homologous recombination (FIG. 1C). The donor template was delivered by IDLV (See FIG. 2D), allowing for efficient transduction of CD34+ HSPCs with minimal cytotoxicity, transiently producing high template copy numbers with minimal genomic integration.

Figure 3A:
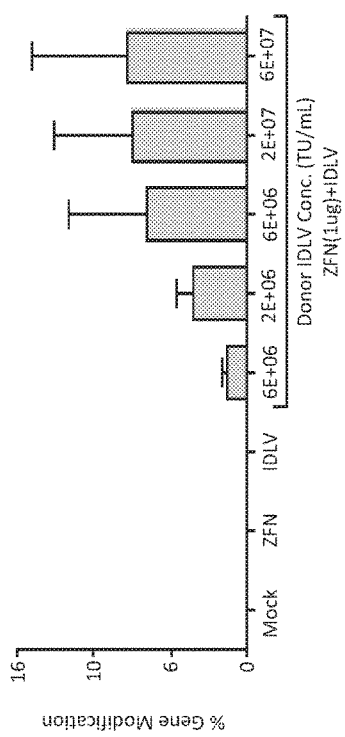
FIGS. 3A through 3C are graphs showing titration of the donor IDLV. CD34+ cells were electroporated with a constant amount of in vitro transcribed ZFN mRNA and transduced with increasing amounts of donor IDLV. Mock indicates untreated cells, ZFN only sample electroporated with 10 ug/mL of each ZFN, IDLV only sample pulsed and transduced with 6E+07 TU/ml of donor IDLV.
Figure 3B:
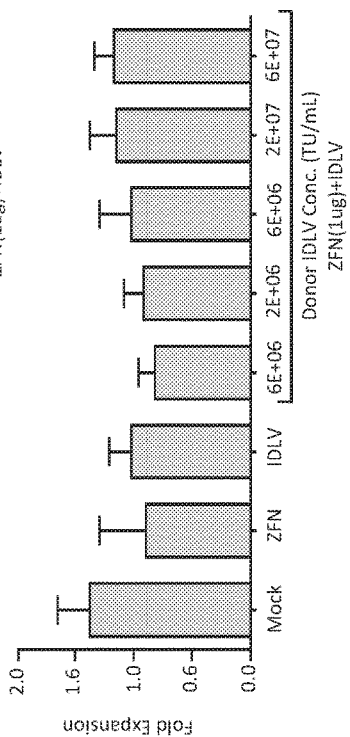
Figure 3C:
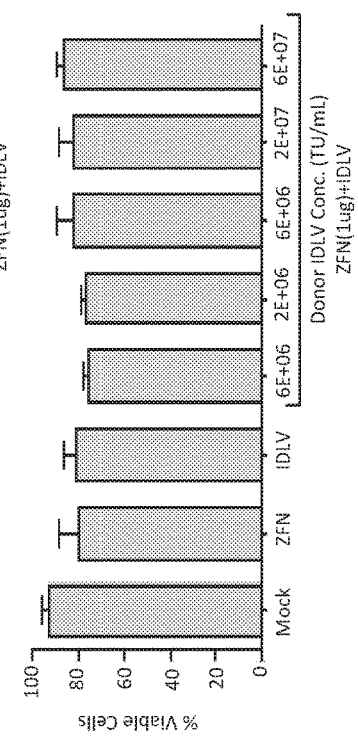

Gene modification levels in the CD34+ cells treated with the ZFN (pair 33488/33501) plus the IDLV donor were initially determined by the HhaI RFLP digestion (FIG. 1D) and a quantitative PCR-based (qPCR) assay at an average of 18.0±2.2% of alleles (FIG. 1E). Optimizations of ZFN mRNA and IDLV donor concentrations were performed (FIG. 2 and FIG. 3) and demonstrated the importance of titrating the ZFN reagents in the cell type of interest to achieve high-level modification while maintaining cell numbers and viability.

Use of an oligonucleotide as a gene modification/correction template would have advantages of speed, cost, reproducibility, and ease of experimentation. Initial experiments using the oligonucelotide donor template in HSPCs from mPB introduced a 3 base pair sequence designed to create an AvrII RFLP in the beta-globin gene (HBB) yielded 15% gene modification (See FIG. 4).

To refine the use of oligo donors, a panel of oligonucleotides corresponding to one or the other strand and of symmetrically increasing length centered on the ZFN cleavage site was tested (see Table 4 below), where bold indicates the base that was mutated with respect to the wild type sequence. The oligonucleotides that are labeled with an 's' comprise sequences designed to introduce the sickle mutation into a wild type gene. As shown in the table, in the column labeled 'S', the wild type sequence comprises an A at this position while the sickle mutation comprises a T.

Figures 17A, 17B:
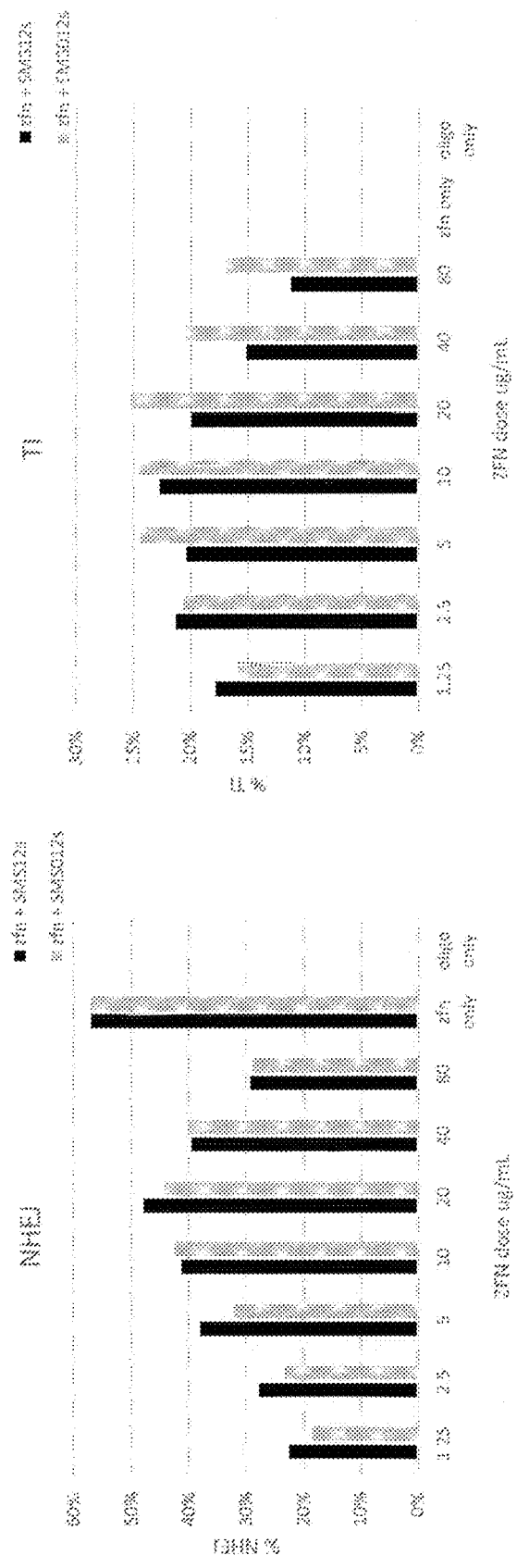
FIGS. 17A and 17B show correction at the beta-globin locus in CD34+ cells using oligonucleotide donors and varying concentrations of the zinc-finger nuclease pair 47773/47817.

At high ZFN mRNA (pair 47773/47817) concentrations use of a donor oligonucleotide containing SMS012 yielded more HBB-modified alleles than use of the SMS12 donor (FIG. 17B).

Comprehensive analysis of molecular outcomes at HBB after treatment with ZFNs and the SMS124 donor revealed only minor levels of unexpected DNA repair events such as those from a combination of homology-directed and NHEJ-based gene modification (1.5%) or from NHEJ-based capture of the oligonucleotide (0.4%) (See Table 5 below).

TABLE 5

Molecular outcomes from treatment of HSPCs with ZFN and oligonucleotide donor

| Outcome | Frequency (%) |
| --- | --- |
| No change | 46.1 |
| NHEJ-mediated deletions | 30.5 |
| Oligonucleotide-templated gene modification | 18.8 |
| NHEJ-mediated insertions | 2.8 |
| Half gene modification, half NHEJ | 1.5 |
| Capture of the donor oligonucleotide | 0.4 |

Finally, the overabundance of partial homology-directed gene modification events (SMS12 versus SMS24) lent strong support to the idea that new DNA synthesis during

TABLE 4

Oligo donors

| SMS position | S | 0 | | 1 | | 2 | 3 | | | 4 | | | 5 | | SEQ ID NO |
| --- | --- | --- | --- | --- | --- | --- | --- | --- | --- | --- | --- | --- | --- | --- | --- |
| WT | G | A | G | G | A | G | A | A | G | T | C | T | G | C | C | G | T | T | 60 |
| SMS1 | G | A | G | G | A | A | A | A | G | T | C | T | G | C | C | G | T | T | 61 |
| SMS2 | G | A | G | G | A | G | A | A | A | T | C | T | G | C | C | G | T | T | 62 |
| SMS4 | G | A | G | G | A | G | A | A | G | T | C | T | G | C | T | G | T | T | 63 |
| SMS12 | G | A | G | G | A | A | A | A | A | T | C | T | G | C | C | G | T | T | 64 |
| SMS14 | G | A | G | G | A | A | A | A | G | T | C | T | G | C | T | G | T | T | 65 |
| SMS24 | G | A | G | G | A | G | A | A | A | T | C | T | G | C | T | G | T | T | 66 |
| SMS124 | G | A | G | G | A | A | A | A | A | T | C | T | G | C | T | G | T | T | 67 |
| SMS012 | G | A | A | G | A | A | A | A | A | T | C | T | G | C | C | G | T | T | 68 |
| SMS12s | G | T | G | G | A | A | A | A | A | T | C | T | G | C | C | G | T | T | 69 |
| SMS012s | G | T | A | G | A | A | A | A | A | T | C | T | G | C | C | G | T | T | 70 |

Figure 5:
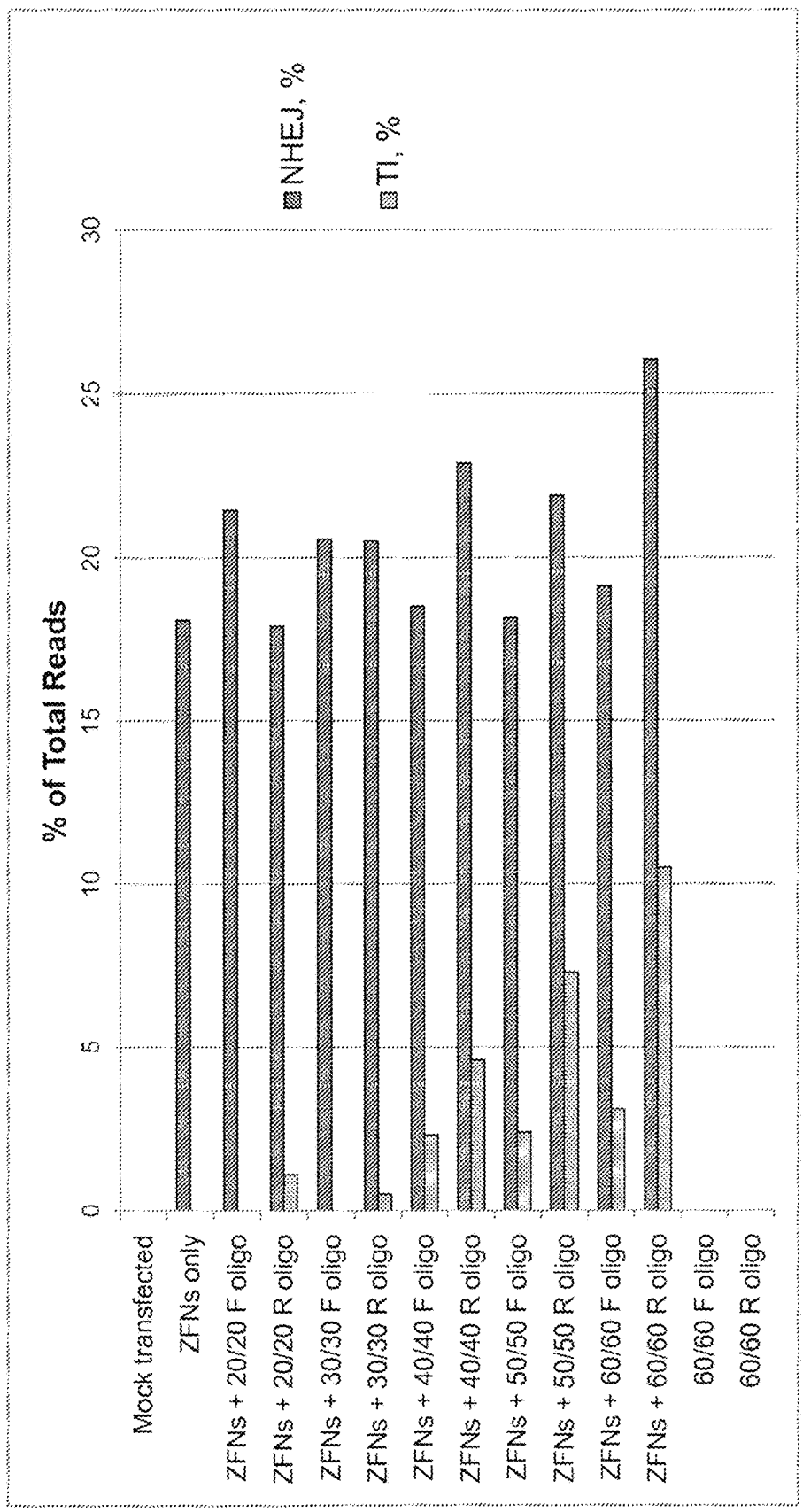
FIG. 5 shows optimization of donor length and strand. mPB CD34+ cells were transfected with combinations of ZFNs and oligonucleotides designed to introduce a three base pair sequence into the beta-globin locus. Cells were harvested and the levels of NHEJ-driven indels and targeted integration ("TI") of this short sequence were assayed by high-throughput DNA sequencing (HTS). Approximately 4-9,000 sequence reads were obtained per sample.

Use of longer, reverse-strand oligonucleotides gave the highest level of gene modification (See FIG. 5). Since gene modification or correction at the SCD mutation site will not change the sequence or spacing of the ZFN binding sites, silent mutations were designed into the donor template and co-introduced into the chromosome to prevent or reduce ZFN binding and re-cleavage of modified alleles. Use of reverse-strand donors is compatible with introduction of silent mutations at the 3' ZFN binding site (FIG. 4C).

Various combinations of silent mutations were introduced into the donor oligo, and the frequency of gene modification was assayed. Combination of silent mutation sites (SMS) one and two (SMS12) yielded the highest level of HBB modification and was used in all subsequence subsequent experiments (FIG. 4D). The inverse relationship between gene-modified HBB alleles and modified-then-re-cleaved alleles suggests that the SMS donors indeed serve to block ZFN re-cleavage (FIG. 4E). Examination of HBB transcripts in HSPC pools and in burst-forming unit, erythroid colonies (BFU-E) found no evidence for alteration of splicing of mRNA from any SMS allele.

oligonucleotide-templated gene modification occurs using the left-hand 3' single-stranded end of the resected DSB (see FIG. 6). Optimal combinations of ZFNs, oligonucleotide, and HSPC donor allowed gene modification of 30-40% of alleles (see FIG. 4F).

Thus, ZFNs are able to induce both high levels of targeted DSBs as well as high levels of site-specific gene modification in primary HSPCs when delivered alongside a homologous donor template.

Example 5: ZFN Specificity

Since beta-globin has high homology to other globin genes (delta-, epsilon-, A gamma-, G gamma-, and pseudo-beta-globin), the ZFNs were designed to avoid cleavage in these regions (FIG. 6A). Cleavage rates at homologous globin genes using the 33488/33501 pair were assayed using the Surveyor nuclease assay and by high-throughput DNA sequencing. Analysis of each of these regions revealed off-target modification at only the highly-homologous delta-globin gene in mPB, CB, and SCD BM CD34+ cells (FIG.

6B, Table 3). We complemented these direct tests of off-target ZFN cleavage with a more comprehensive, unbiased genome-wide approach to identify off-target sites. This assay is based on the propensity of a non-homologous IDLV to be captured at the sites of double-stranded breaks and uses downstream clustered integration site analysis (CLIS) of the integrations in K562 cells selected for their permissiveness to IDLV capture. The procedure followed is outlined below:

Beta-globin gene cluster sites were PCR-amplified with the following primers: HBD: 5'-ggttcatttttcattctcaca-3' (SEQ ID NO:41) and 5'-gtaatctgagggtaggaaaac-3' (SEQ ID NO:42); HBBP1: 5'-cacccttgaccaatagattc-3' (SEQ ID NO:52) and 5'-gagactgtgggatagtcata-3' (SEQ ID NO:43); HBE1: 5'-cattatcacaaacttagtgtcc-3' (SEQ ID NO:44) and 5'-agtctatgaaatgacaccatat-3' (SEQ ID NO:45); HBG1: 5'-gcaaaggctataaaaaaaattagc-3' (SEQ ID NO:46) and 5'-gagatcatccaggtgctttg-3' (SEQ ID NO:47); HBG2: 5'-ggcaaaggctataaaaaaaattaagca-3' (SEQ ID NO:48) and 5'-gagatcatccaggtgcttta-3' (SEQ ID NO:49) and analyzed by Surveyor® Nuclease as described above.

Figures 7A, 7B:
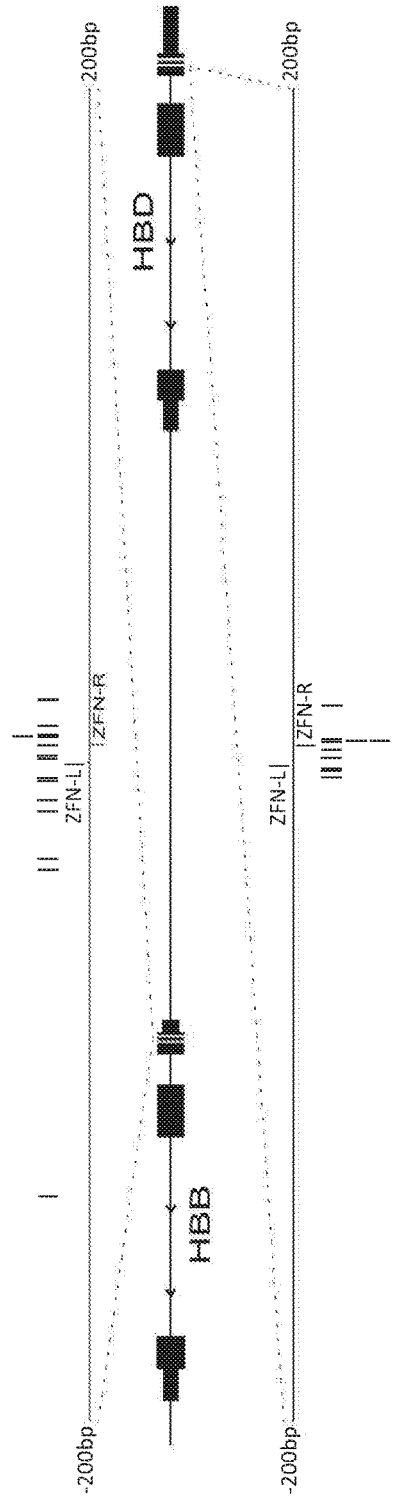
Figure 8:
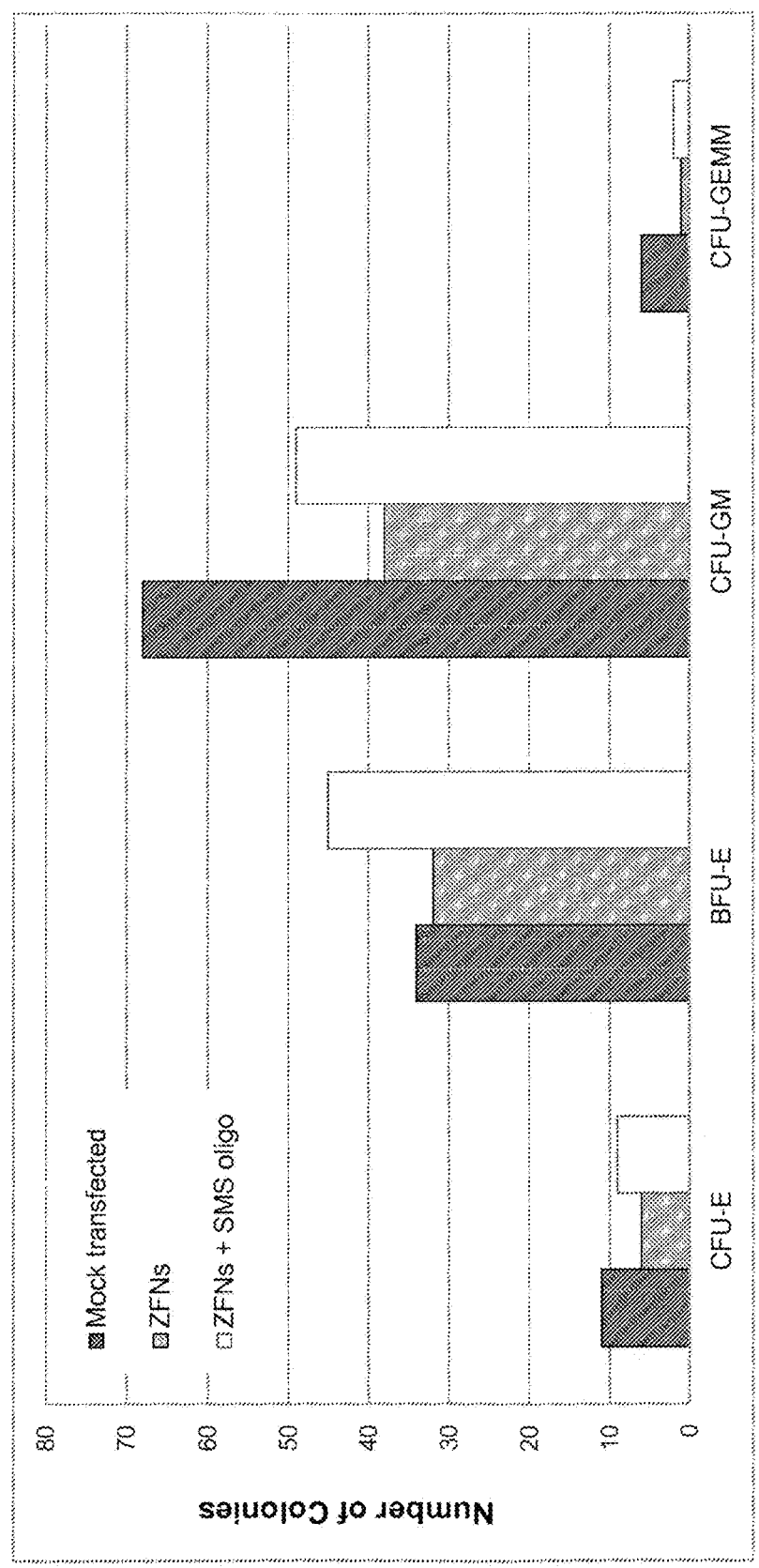
FIG. 8 is a graph showing the colony-forming potential of ZFN and oligonucleotide modified HSPCs. mPB CD34+ cells were either mock transfected, transfected with 10 ug/mL ZFNs, or transfected with ZFNs and an oligonucleotide donor at 3 µM. After five days of culture, cells were plated in methylcellulose and cytokine-containing medium and differentiated. After fifteen days of growth colony-forming units (CFU) were counted and classified morphologically as either erythroid (E), burst-forming units—erythroid (BFU-E), granulocyte/macrophage (GM), or granulocyte/erythroid/macrophage/megakaryocyte (GEMM).

K562 cells were electroporated with 15 µg/mL of ZFN mRNA and transduced with 2E+08 T U/mL (MOI=250) of an IDLV containing a GFP transgene driven by the MND promoter (see Challita, P. M. et al. (1995) *J of Virol* 69, 748-55) and lacking any homology to the beta-globin locus to ensure that integration at double stranded breaks was due to NHEJ-mediated capture (See FIG. 7A). Four individual biological replicates of ZFN+IDLV were completed to maintain high sensitivity to potential genome-wide off-target sites while two controls were completed to determine the level of background integration. Control cells received the GFP IDLV, but no ZFN mRNA to detect sites of naturally occurring DSBs that capture the IDLV without the action of ZFNs. The K562 cells were cultured in RPMI1640 (Cellgro) with 10% fetal bovine serum (Gemini Bio-products) and 1% Penicillin/Streptomycin/L-glutamine (Gemini Bio-products) for 60 days. During this period, flow cytometric analyses for GFP positivity were regularly performed to ensure any non-integrated IDLV was diluted out of the samples. On day 60, the samples were sorted by fluorescence-activated cell sorting (FACS) to isolate the GFP+ cells, expanded for 5 days, genomic DNA was extracted, and samples were prepared for sequencing of vector integration sites by nonrestrictive Linear Amplification Mediated-PCR35. Clustered integration site (CLIS) analysis was performed as outlined previously (Gabriel, R., et al (2011) *Nat Biotech.* 29(9):816-23) with a CLIS window of 500 base pairs to reveal sites of ZFN cleavage. All CLIS were analyzed to determine the level of homology of each site to the ZFN pair sequences. Percentage of homology was defined as the number of matching base pairs at the site to all iterations of ZFN binding (homodimers and heterodimers) with spacer lengths of up to 20 nucleotides. The highest percentage homology for each CLIS is reported below in Table 6. For this table, all identified CLIS are listed with their highest percentage of homology to the ZFN target site within 200 base pairs of their integration site. All possible iterations of ZFN binding (heterodimers and homodimers) were assessed and spacer lengths of up to 20 nt were analyzed. The two ZFN sites of cleavage are highlighted in bold. All other fragile sites identified by CLIS are italicized. Chr, chromosome; CLIS, clustered integration site; L, 'left' ZFN monomer (SBS#33488); R, 'right' ZFN monomer (SBS#33501); while the number in ZFN dimer corresponds to spacer size that gave the greatest percentage of homology to the ZFN target site. 20,000 random genomic sites were analyzed using this method to determine the background level of ZFN homology across the genome.

TABLE 6

| CLIS and percentage of homology to ZFN target site | | | | | |
|---|---|---|---|---|---|
| Chr Location | Nearest RefSeq Gene (within 500 kb) | Identity (%) | # of CLIS | ZFN dimer | Sample |
| 11 5248238 | HBB | 100% | 18 | L_5_R | ZFN + GFP |
| 11 5255649 | HBD | 91% | 10 | L_5_R | ZFN + GFP |
| *7 12238685* | *TMEM106b* | *52.94%* | *3* | *L_12_R* | *ZFN + GFP* |
| *19 58024409* | *ZNF773* | *62.50%* | *6* | *L_18_L* | *ZFN + GFP; GFPonly* |
| *1 121484829* | *EMBP1* | *55.88%* | *6* | *R_14_L* | *ZFN + GFP; GFPonly* |
| *10 117392565* | *ATRNL1* | *55.88%* | *3* | *L_15_R* | *ZFN + GFP; GFPonly* |
| *19 27733086* | *—* | *56.25%* | *3* | *L_17_L* | *GFP only* |
| *12 112392669* | *TMEM116* | *52.94%* | *2* | *L_4_R* | *GFP only* |
| *12 693139* | *NIN.I2* | *35.29%* | *2* | *L_1_R* | *GFP only* |
| *16 46428309* | *ANKRD26P1* | *53.12%* | *2* | *L_3_L* | *GFP only* |
| *5 144123495* | *KCTD16* | *53.12%* | *2* | *L_4_L* | *GFP only* |
| *3 183525263* | *YEATS2* | *53.13%* | *2* | *L_15_L* | *GFP only* |
| *5 53018665* | *NDUFS4* | *58.82%* | *2* | *R_9_L* | *GFP only* |
| *3 19674417* | *EFH8* | *56.25%* | *2* | *L_9_L* | *GFP only* |
| *9 127395708* | *NR6A1* | *55.88%* | *2* | *L_6_R* | *GFP only* |
| *7 137218714* | *DGKI* | *52.94%* | *2* | *L_12_R* | *GFP only* |

As predicted, the CLIS analysis revealed trapping at beta-globin and delta-globin (FIG. 7, Table 6). No other putative off-target sites in the CLIS analysis that had significant homology to the ZFN binding sites were found.

These results demonstrate the high level of specificity of this pair of ZFNs to their intended target site on a genome-wide scale.

Example 6: In Vitro Differentiation of Modified HSPC

To ensure that gene-modified HSPCs were capable of a normal, broad spectrum of erythroid and myeloid differentiation, treated cells were assayed both as single cells and in bulk culture. Single-cells were monitored for colony-forming potential in methylcellulose medium containing cytokines that promote HSPC differentiation. Briefly, one day post electroporation, 100 and 300 viable cells were plated per 35 mm cell culture dish in duplicate in MethoCult™ Optimum methylcellulose-based media (Stem Cell Technologies). For experiments with oligonucleotide donors, cells were plated five days post-electroporation. Following two weeks in culture at 5% CO2, 37° C. and humidified atmosphere, the different types of colonies were characterized and enumerated based on their morphology. HSPCs treated with either ZFNs alone (pair 33488/33501) or treated with ZFNs and an oligonucleotide donor generated similar numbers and patterns of erythroid and myeloid clones.

The in vitro erythroid differentiation technique for SCD BM samples was adapted from Giarratana et al. ((2005) *Nat Biotech* 23:69-74) and described in Romero and Urbinati et al ((2013) *J Clin Invest* 123(8): 3317-3330). One day after electroporation, cells were placed in erythroid culture. In order to obtain high numbers of cells for downstream analyses, cells were placed in co-culture on day 12 of the protocol as opposed to day 8 to allow for increased erythroid expansion. Cells were harvested on day 22 of the experiment, pelleted, and subjected to HPLC analysis (see below). Assay of HBB splicing was also performed by RT-PCR using 5'-acatttgcttctgacacaac-3' (exon 1, SEQ ID NO:50)

and 5'-gaaattggacagcaagaaagc-3' (exon 3, SEQ ID NO:51) and no exon skipping or intron retention was observed.

Genotyping of individual erythroid colonies confirmed the presence of the intended edits at the expected frequency. In addition, HSPCs were induced to differentiate to red blood cells in bulk culture (Giarratana, M. et al. (2011) Blood 118, 5071-9). Cells were sampled throughout red blood cell differentiation and the frequency of edited cells measured by high-throughput DNA sequencing. Consistent with our single-cell analysis of erythroid colonies grown in methylcellulose, essentially no change in the frequency of modified cells was found during differentiation to red blood cells in bulk culture regardless of the starting level of gene modification in the pool (FIG. 9A).

Figures 9A, 9B:
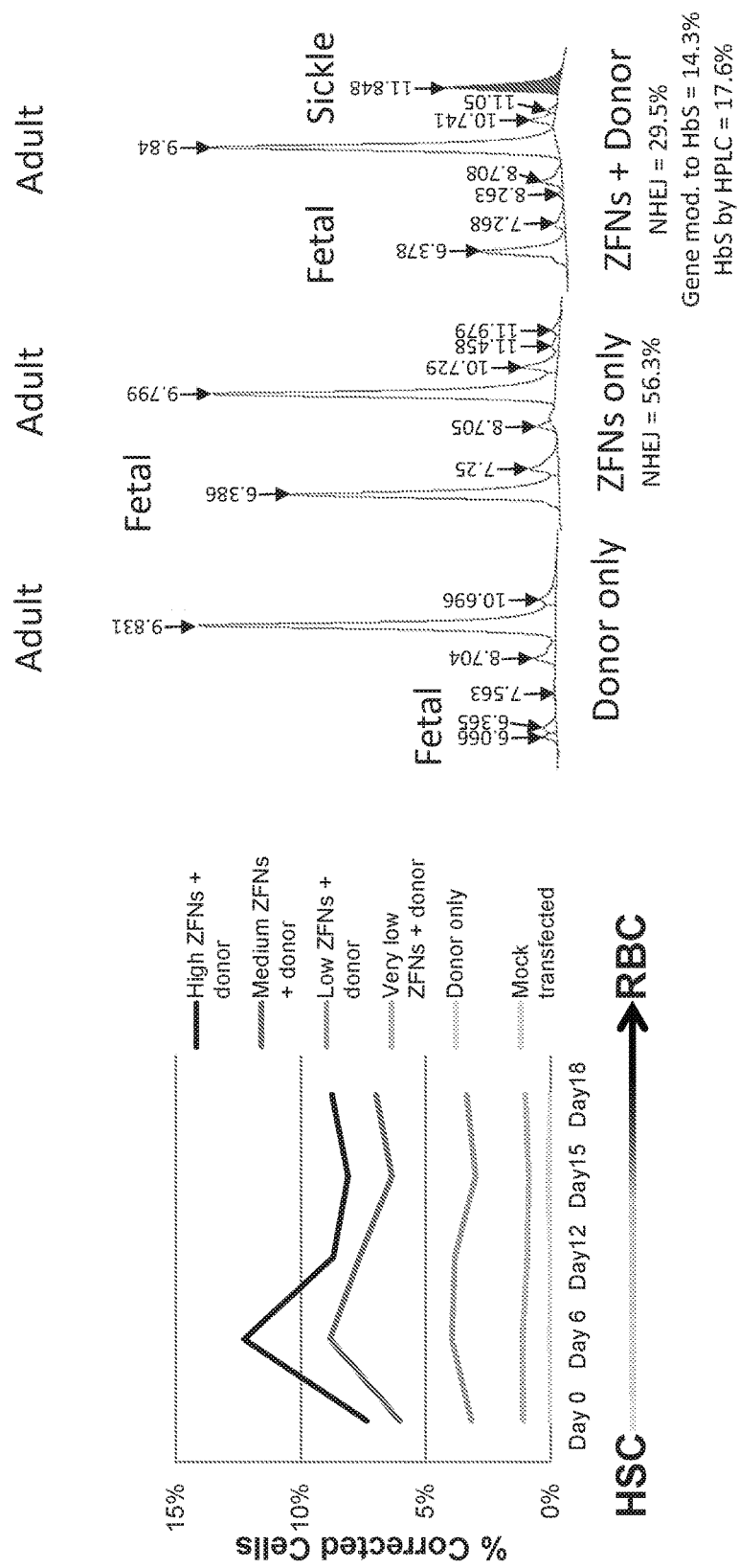
FIGS. 9A and 9B show the stability of modified cells during erythroid differentiation.
Figure 12A:
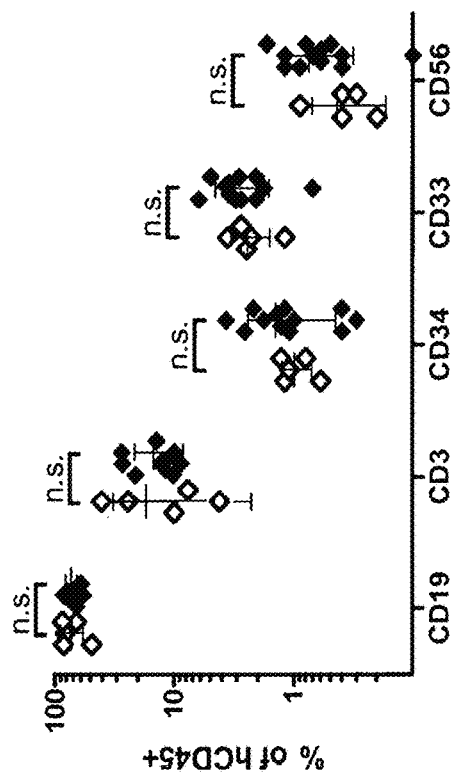
FIGS. 12A through 12D show the final peripheral blood engraftment and lineage analysis.
Figure 12B:
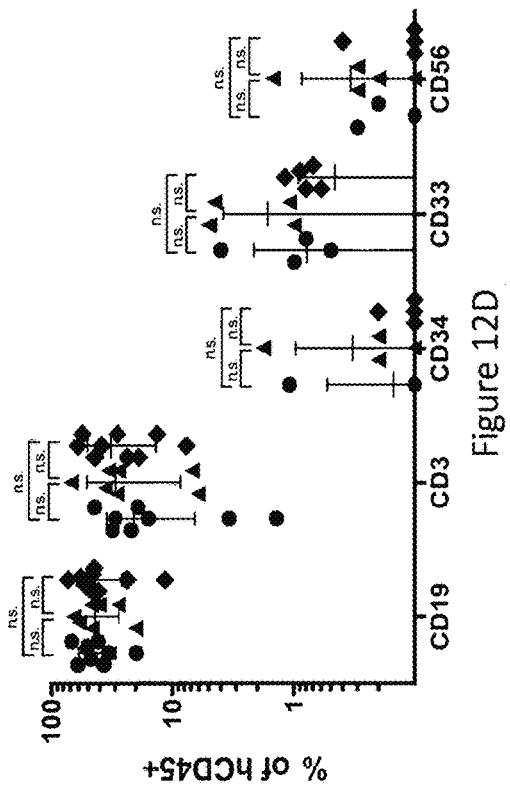
Figure 12C:
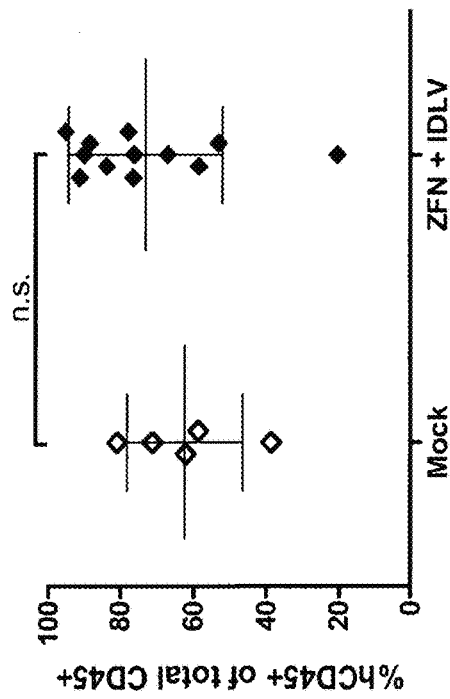
Figure 12D:
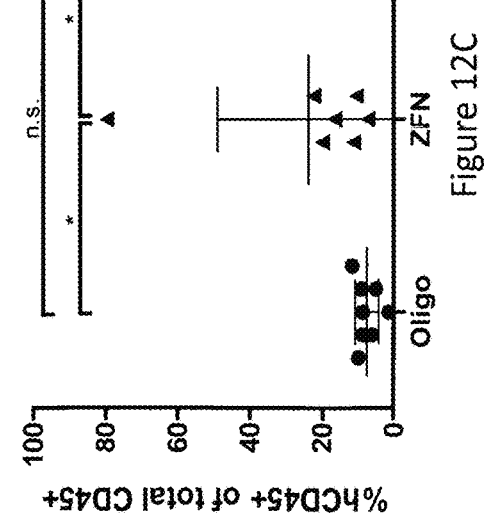

For analysis of the globin chains, HPLC was performed (FIG. 9B). For SCD BM samples, HPLC of hemoglobin (Hb) species produced by terminal stage erythroid cells was performed as described in Wilber, A. el ul. ((2011) Blood 117:2817-26) with some slight modification. Erythroid cells (1-2E+07) were harvested at the conclusion of the erythroid culture (day 22), pelleted, and stored frozen at −80° C. until lysis. Upon thawing, cells were re-suspended in 25 uL of hemolysate reagent (Helena Laboratories) and refrigerated overnight before centrifuging at 20,800×g for 10 minutes at 4° C. to remove cellular debris. The cleared supernatant was used for characterization of Hb production by HPLC using a cation-exchange column (Ultra2 Variant Resolution Analyzer; Primus Diagnostics) and calibrated samples for human hemoglobins. Peaks corresponding to Hb species were identified based on retention time with software accompanying the HPLC instrument. The relative percentage of HbA produced for each sample was calculated based on the sum total of areas under the curve for each of the primary hemoglobin peaks which included acetylated fetal hemoglobin, HbFAc; fetal hemoglobin, HbF; wild-type hemoglobin, HbA; and sickle hemoglobin, HbS.

For mPB samples, erythroid cells were harvested at day 18 of the erythroid culture. Cells were pelleted and lysed in water for 10 min at RT. After centrifugation at 20,000 g for 5 minutes to remove cellular debris, cell lysates were stored frozen at −80° C. Upon thawing, cell lysates were diluted 1:10 in mobile phase A and characterized by HPLC (Infinity 1260, Agilent) using a weak cation-exchange column (Poly-CAT ATM, PolyLCINC.). FASC Reference Material (Trinity Biotech) was used to define the elution time of common hemoglobins (HbF, HbA, HbS, HbC). Analysis and peak integration was performed using OpenLAB CDS Chemstation software. The relative percentage of HbA produced for each sample was calculated based on the sum total of areas under the curve for each of the hemoglobin peaks which included acetylated fetal hemoglobin, HbFAc; fetal hemoglobin, HbF; wild-type hemoglobin, HbA; and sickle hemoglobin, HbS.

In a parallel experiment, we converted 14% of HBB alleles to the sickle form and assayed by HPLC the globin chains present after 18 days of erythroid differentiation. Approximately 18% of the hemoglobin produced by these cells was sickle hemoglobin demonstrating the impact of the gene modification event at the protein level (FIG. 9B).

Example 7: Engraftment of Modified Cells into Mice

To determine whether the ZFN-modified cells maintain their hematopoietic repopulating capacity, ZFN- and donor-treated or mock-treated CB-derived HSPCs were xenografted into immune-deficient NSG mice.

Briefly, fresh CB CD34+ cells from multiple healthy individuals were pre-stimulated for 2 days before being electroporated with ZFN mRNA and transduced with donor IDLV (2E+07TU/mL; MOI=50). The pre-stimulation medium including X-VIVO15 media (Lonza) containing glutamine, penicillin, streptomycin, 50 ng/ml SCF, 50 ng/ml Flt-3 and 50 ng/ml TPO (Peprotech) was used. Following one day of recovery, 1E+06 viable cells in PBS (Corning) with 0.1% BSA (Sigma) were transplanted by tail-vein injection into 6- to 8-week-old, NSG mice (The Jackson Laboratory) after 250 cGy total body irradiation. Control samples of CD34+ cells that were cultured in parallel but not exposed to mRNA, electroporation, or IDLV (mock-treated) were used. Small aliquots were cultured in vitro for multiple analyses. mPB samples were frozen one day following electroporation, thawed at a later date and allowed one day of recovery as above before transplantation.

Engraftment of human cells was evaluated by flow cytometry at weeks 5 post-transplant using V450-conjugated anti-human CD45 vs APC-conjugated anti-murine CD45. After incubation with the antibodies, red blood cells were lysed with BD FACS-Lysing Solution (BD Biosciences). The percentage of engraftment was defined as % huCD45+/(% huCD45++ % muCD45+). Engraftment and lineage distribution in the peripheral blood and BM were evaluated by flow cytometry at 8 weeks and 16 weeks post-transplant using V450-conjugated anti-human CD45, V500-conjugated anti-murine CD45, FITC-conjugated anti-human CD33, PerCP-conjugated anti-human CD3, PE-conjugated anti-human CD56, PE-Cy7-conjugated anti-human CD19, and APC-conjugated anti-human CD34 (all antibodies BD Biosciences).

Descriptive statistics including mean and standard deviation for outcome variables were both reported and presented graphically. For quantitative outcomes related to gene modification levels, engraftments and lineages, pairwise comparison was performed by either unpaired t-test or within the framework of one-way ANOVA if there were more than two groups. Dose-response analysis was performed to evaluate ZFN and donor ratio optimization. Specifically, we used a linear mixed model approach but treated dose as continuous and fixed effect and experiment as random effect. Fold expansion of SCD patient BM cells over time was assessed by repeated measure ANOVA. In our statistical investigation, hypothesis testing was two-sided, and a significance threshold 0.05 for p-value was used. All statistical analyses were carried out using SAS version 9.3 (SAS Institute Inc. 2012).

Parallel culture of the cells in vitro showed that gene modification rates ranged from 5%-20% by qPCR RFLP analysis, with a mean value of 14.5±6.4% (FIG. 10). High-throughput sequencing revealed 10.5±4.0% of alleles contained the exchanged base at the sickle location with insertions or deletions (indels) seen in 32.0±9.9%. In addition, the hematopoietic potential of these cells was evaluated in an in vitro colony-forming assay; the cells maintained their broad-spectrum colony-forming ability relative to untreated mock samples in all analyzable lineages.

At 5 and 8 weeks post injection, the transplanted mice were evaluated for engraftment of human HSPCs measured as the percentage of human CD45+ cells out of total CD45+ cells, both human and murine. Engraftment levels of ZFN and IDLV-treated HSPCs were comparable to those of untreated controls with an average of 14.8±11.4% at week 5 and increased to 45% at week 8 (FIG. 10C). Lineage analysis (CD3 for T cells, CD33 for myeloid cells, CD34 for HSPCs, CD19 for B cells, and CD56 for NK cells) of the peripheral blood of the mice was as expected in this model (FIG. 11). Analysis of the human cells in mice receiving cells treated with both ZFN and an oligonucleotide donor revealed an HSPC differentiation spectrum similar to that of the ZFN and IDLV-treated HSPCs (FIG. 10E).

Mice were euthanized at 16 weeks post-transplant to allow for evaluation of human cell engraftment and gene modification levels. For the mice receiving ZFN and IDLV-treated cells, evaluation of the peripheral blood revealed high levels of engraftment and expected lineage distribution. Analysis of the bone marrow (BM) compartment was similar (FIG. 12). Likewise, in mice that received cells treated with both ZFNs and oligonucleotide, engraftment levels and lineage distribution were similar to those seen in the cohort of mice receiving ZFN and IDLV-treated HSPCs in the peripheral blood and BM.

Figure 13A:
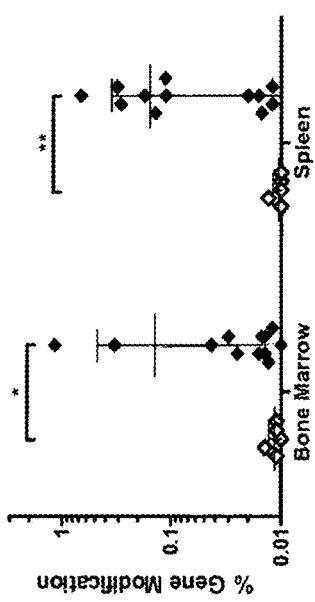
FIGS. 13A through 13C show that gene modified cells persist in NSG mice.
Figure 13B:
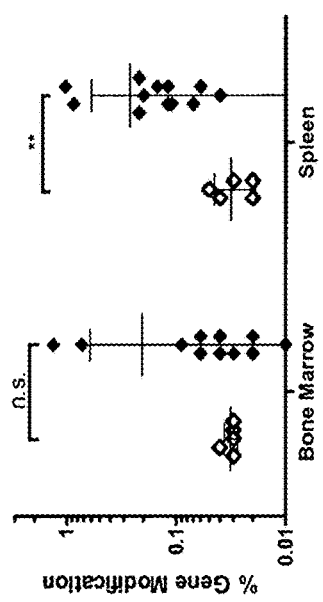

To determine whether the human cells present in the mice were indeed those modified by the ZFN reagents, genomic DNA was isolated from BM and spleen tissues of each mouse and the human beta-globin gene was interrogated. Analysis of the HhaI RFLP by qPCR in the tissues of mice receiving ZFN and IDLV-treated cells revealed the presence of gene modification in these mice, though lower frequency (0.14±0.32% and 0.16±0.18% for BM and spleen, respectively) than the 10.5% gene modification levels observed for input cells (FIG. 13). Sequence analysis confirmed gene modification at the sickle mutation in human cells in the BM and spleen with comparable averages at 0.21±0.39% and 0.27±0.31%, respectively (FIG. 13B). Analysis of the insertions and deletions (indels) caused by NHEJ at the cut site revealed higher levels of changes than by HDR, with 4.8±7.8% of all sequence reads from in the BM containing indels and 3.8±3.7% from in the spleens (FIG. 14).

Figure 13C:
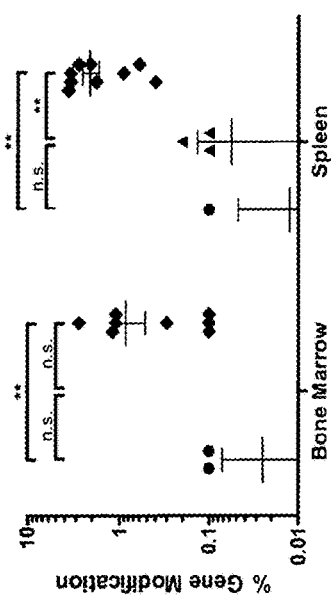
Figure 14A:
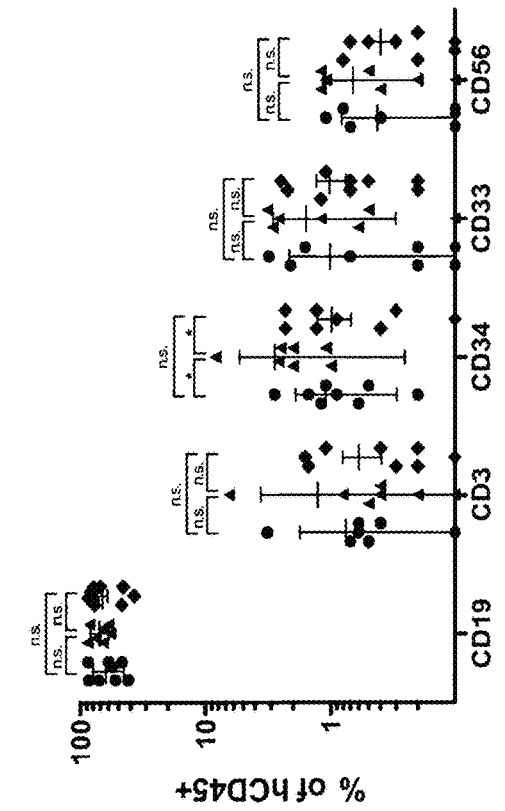
FIGS. 14A through 14D show the final bone marrow engraftment and lineage analysis.
Figure 14B:
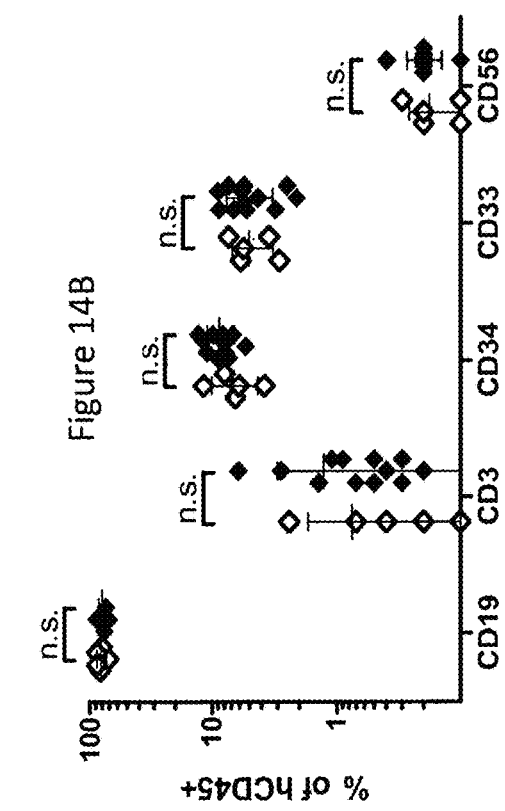
Figure 14C:
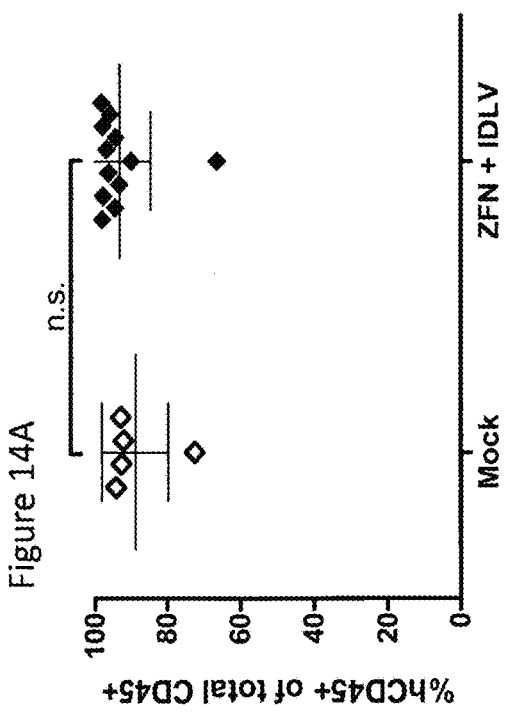
Figure 14D:
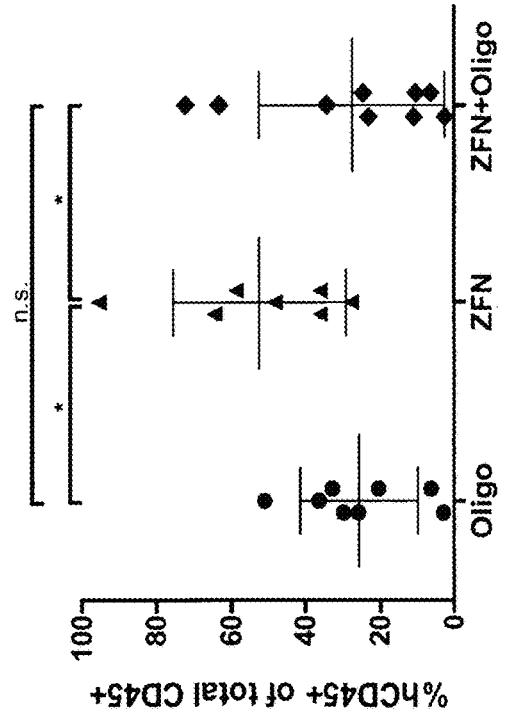

Genomic analysis of the BM and spleens of mice receiving ZFN and oligonucleotide-treated cells bearing 17.3% gene modification at the sickle base and 19.8% indels in the bulk population prior to administration also demonstrated maintenance of gene modification. DNA from these tissues was subjected to high-throughput sequencing, revealing 0.85±0.81% and 2.11±1.19% targeted gene modification in the BM and spleen, respectively (FIG. 13C). Assessment of the indels in these tissues showed levels of 3.34±2.65% in the BM and 5.86±2.30% in the spleen (FIG. 14).

These results demonstrate that CD34+ cells that have undergone site-specific DNA cleavage by ZFNs and homology-directed gene modification are capable of engrafting and undergoing multi-lineage differentiation.

Example 8: Gene Correction in Sickle Bone Marrow

Figure 15A:
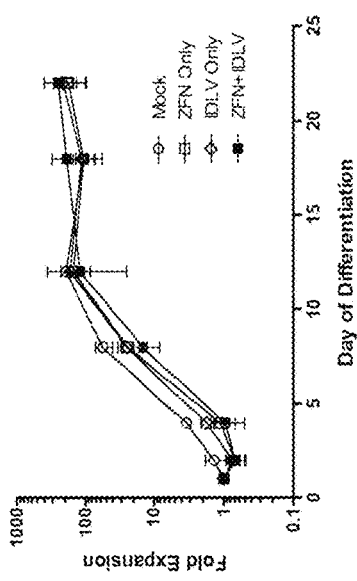
FIGS. 15A through 15C show differentiation of sickle bone marrow CD34+ cells.
Figure 15B:
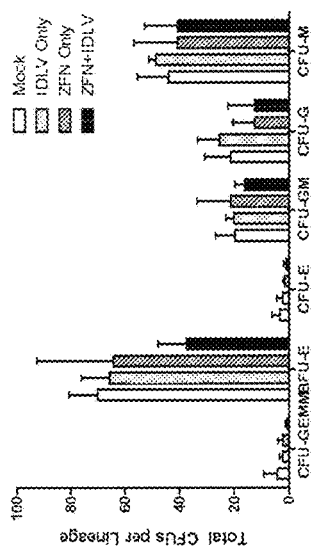
Figure 15C:
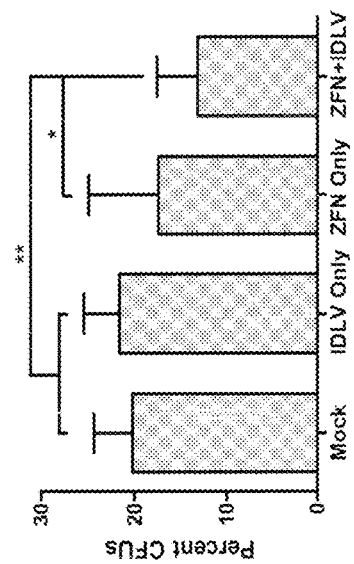

Since sickle-cell disease patients are not candidates for stem cell mobilization with G-CSF, we obtained CD34+ HSPCs from BM aspirates of these patients. Site-specific gene correction was performed using ZFN mRNA and the IDLV donor. Cells were placed in an erythroid expansion medium and subsequently differentiated using an established method (Romero et al, ibid, Giarratana et al, ibid). In addition, a portion of the cells were evaluated for their colony-forming potential. The cells treated with ZFN+IDLV (pair 33488/33501) showed modestly lower (35%) colony-forming ability compared to mock, non-electroporated control samples (FIG. 15).

Following the initial erythroid expansion (but before enucleation) cells were harvested for genomic analysis. RFLP analysis by qPCR of these samples revealed gene modification levels that averaged 20.1±8.8% (FIG. 16A). These results were confirmed by deep sequencing, showing correction of the SCD mutation in 18.4±6.7% of the reads (FIG. 16B). Additionally, sequencing confirmed that most alleles containing the correction of the SCD mutation also contained a base change at the HhaI location, indicating that most of HDR-driven events encompass at least the 22 bp distance between those two bases. Following the conclusion of the erythroid culture, samples were collected for analysis of the globin tetramers by high pressure liquid chromatography (HPLC) (FIG. 16C).

The presence of an HbA peak in erythroid cells derived from the ZFN and IDLV-treated samples demonstrates that the gene correction led to functional conversion of the betaS allele to a betaA allele. No such peak was seen in erythrocytes derived from mock-treated cells. The HbF peak showed a relative increase due to the decrease in the HbS peak in the ZFN treated samples. The relative induction of HbA in ZFN and IDLV-treated samples averaged 5.3±0.02%, with protein correction levels up to 10.0% (FIG. 16D).

These results demonstrate the ability of the ZFNs in combination with an IDLV donor to correct the phenotype of HSPCs from the bone marrow of sickle-cell disease patients.

The results shown here demonstrate high levels of gene correction of the sickle-cell disease mutation in human hematopoietic stem/progenitor cells using zinc-finger nucleases in vitro. In the present study, we designed ZFN pairs to cleave the beta-globin locus. In combination with a homologous donor template (delivered as either an oligonucleotide or via an integrase-defective lentiviral vector), these ZFNs are able to induce homology-directed repair at high levels in progenitor cells.

Analysis of the ZFN cleavage sites revealed that the large majority of nuclease activity took place at the beta-globin locus target site, with a smaller fraction of cleavage at the homologous delta-globin gene. Due to the low level of delta-globin expression in adult erythroid cells (<3.5% of all globin), ZFN activity at this gene in a subset of cells is unlikely to be detrimental. An unbiased, genome-wide evaluation of ZFN off-target cleavage sites in K562 cells using IDLV end-capture demonstrated the high specificity of the ZFNs, with only background integration into naturally fragile sites seen.

When the ZFN and donor-treated cells were transplanted into mice, engraftment and the lineage distribution of the cells were equivalent between mock-treated and ZFN and donor-treated samples. However, despite average levels of gene modification of 10-20% in the in vitro samples before transplantation, the gene correction levels in the human cells in the spleens and BM of the mice after 16 weeks of engraftment were markedly lower. These findings are consistent with recently published work in the field (Genovese et al (2014) *Nature* 510: 235-240) and may imply that while more mature progenitor cells are corrected efficiently, sustained benefit (e.g., clinical benefit) is provided by modification of the earlier, more primitive hematopoietic stem cells.

The efficiency of homology-directed gene correction in more primitive HSPCs as compared to the efficiency of site-specific gene disruption (see Holt et al (2010) *Nat biotech* 28(8):839-47 regarding CCR5 disruption-) may be due to the difference in using a donor template containing the corrective bases, which is co-delivered and cellular DNA damage repair pathways must resolve the DSB using HDR rather than NHEJ. As NHEJ is favored in quiescent, primitive HSC (see Mohrin et al (2010) *Cell stem cell* 7:174-85), a bias in repair pathway choice might limit gene correction in primitive HSCs. Thus, without being bound by one theory, it is possible that the ZFNs are acting with similar efficiency in the mature and primitive cell populations, but the active repair pathway in each cell type differs such that HDR is more active in more mature cells and less so in the primitive HSCs. In particular, cells transplanted into mice maintained their input levels of indels to a greater extent than they did for gene modification (7.4 and 4.3 fold change in indels compared to 43.9 and 11.7 fold change in gene modification for DLV and oligo experiments, respectively).

Experiments in the BM CD34+ cells from sickle-cell disease patients provide promise for clinical translation. Levels of correction of the canonical sickle mutation (at least in erythroid progenitor cells) averaged 18% for these experiments and, upon differentiation, these cells produced corrected, wild-type hemoglobin (HbA). Based on data from allogeneic hematopoietic stem cell transplants for SCD, donor chimerism of 10-30% can result in significant clinical improvement as a result of the selective advantage the normal, donor-derived red blood cells (see Andreani et al (2011) *Chimerism* 2(1):21-22 and Walters et al (2001) *Am Soc Blood and Marrow Transpl* 7:665-73). In addition, heterozygotes for the SCD mutation normally do not experience symptoms of the disease. Thus, correcting only one allele in each HSC may prove sufficient to alleviate a large portion of the symptoms associated with SCD.

Despite recent advances in lentiviral based gene therapy for hemoglobinopathies, and specifically SCD (see Romero et al, ibid, and Chandrakasan and Malik (2014) *Hematol/oncol Clin of North Amer* 28:199-216) potential complications remain due to the need for long-lasting and appropriately regulated expression of the therapeutic transgene. Site-specific correction using targeted nucleases of the canonical A to T disease-causing sickle transversion in HSCs offers the unique ability to maintain expression of beta-globin under its endogenous promoter and locus control region. Further, the genome correction reagents only require a one-time, transient, ex vivo treatment of the cells to result in a permanent correction.

Taken together these data support the continued development of genome editing in HSPCs as a potential treatment for SCD.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An isolated genetically modified human cell comprising a pair of zinc finger nucleases (ZFNs), the pair comprising the zinc finger proteins (ZFPs) designated 47773 and 47817, wherein 47773 binds to a target site within SEQ ID NO:23 and 47817 binds to a SEQ ID NO:24 of an endogenous human beta-hemoglobin (Hbb) gene comprising a sickle cell mutation, wherein the pair of ZFNs makes a genomic modification in the mutant endogenous Hbb gene and the genomic modification comprises insertion of a donor sequence such that the sickle cell mutation is corrected to wild-type Hbb, and the cell expresses wild-type Hbb.

2. The genetically modified cell of claim 1, wherein the cell is a stem cell.

3. The genetically modified cell of claim 2, wherein the stem cell is a hematopoietic stem cell.

4. The genetically modified cell of claim 3, wherein the hematopoietic stem cell is a CD34+ cell.

5. A genetically modified cell descended from the stem cell of claim 2.

6. The genetically modified cell of claim 5, wherein the cell is a red blood cell (RBC).

7. The genetically modified cell of claim 1, wherein the donor sequence encodes a transgene.

8. A pharmaceutical composition comprising the genetically modified cell of claim 1.

9. A method of correcting a sickle cell mutation in an isolated human cell, the method comprising:

introducing a pair of zinc finger nucleases (ZFNs) into an isolated human cell with an endogenous human beta-hemoglobin (Hbb) gene comprising a sickle cell mutation, the pair comprising the zinc finger proteins (ZFPs) designated 47773 and 47817, wherein 47773 binds to a target site within SEQ ID NO: 23 and 47817 binds to a SEQ ID NO: 24 of the endogenous human Hbb gene comprising a sickle cell mutation, and introducing a donor sequence into the isolated human cell, such that the donor sequence is integrated into a double strand break made by the pair of ZFNs, the sickle cell mutation is corrected to wild-type Hbb, and the cell expresses wild-type Hbb.

* * * * *

SEQUENCE LISTING

```
<160> NUMBER OF SEQ ID NOS: 71

<210> SEQ ID NO 1
<211> LENGTH: 25
<212> TYPE: DNA
<213> ORGANISM: Homo sapiens

<400> SEQUENCE: 1
ctgacctctt ctcttcctcc cacag                                     25

<210> SEQ ID NO 2
<211> LENGTH: 13
<212> TYPE: DNA
<213> ORGANISM: Homo sapiens

<400> SEQUENCE: 2
tttctctcca cag                                                  13

<210> SEQ ID NO 3
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tcaaacagac accatggtgc atctgactcc tgaggagaag tctgccgtta ctgccctgtg   60
gggc                                                              64

<210> SEQ ID NO 4
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 4
actcctgagg ag                                                    12

<210> SEQ ID NO 5
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
actcctaggg aggag                                                 15

<210> SEQ ID NO 6
<211> LENGTH: 41
<212> TYPE: DNA
<213> ORGANISM: Homo sapiens

<400> SEQUENCE: 6
caccatggtg catctgactc ctgaggagaa gtctgccgtt a                    41

<210> SEQ ID NO 7
<211> LENGTH: 41
<212> TYPE: DNA
<213> ORGANISM: Homo sapiens

<400> SEQUENCE: 7
caccatggtg catctgactc ctgaggagaa gactgctgtc a                    41

<210> SEQ ID NO 8
<211> LENGTH: 41
<212> TYPE: DNA
<213> ORGANISM: Homo sapiens

<400> SEQUENCE: 8
catcatggtg cattttactg ctgaggagaa ggctgccgtc a                    41

<210> SEQ ID NO 9
<211> LENGTH: 41
<212> TYPE: DNA
<213> ORGANISM: Homo sapiens

<400> SEQUENCE: 9
cactgtagtg catttcactg ctgacaagaa ggctgctgcc a                    41

<210> SEQ ID NO 10
<211> LENGTH: 41
<212> TYPE: DNA
<213> ORGANISM: Homo sapiens

<400> SEQUENCE: 10
cgccatgggt catttcacag aggaggacaa ggctactatc a                    41

<210> SEQ ID NO 11
<211> LENGTH: 41
<212> TYPE: DNA
<213> ORGANISM: Homo sapiens

<400> SEQUENCE: 11
cgccatgggt catttcacag aggaggacaa ggctactatc a                    41

<210> SEQ ID NO 12

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Leu Arg His His Leu Thr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Leu Arg His Asn Leu Arg Ala
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asp Gln Ser Asn Leu Arg Ala
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Asn Ala Ser Arg Thr Arg
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Ser Asp Asn Leu Ser Glu
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17
```

Arg Ser Gln His Arg Lys Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly Ser Leu Ser Arg
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Arg Ser Asp Leu Ser Arg
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Arg Ser Ala Leu Ala Arg
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Ser Ser Asn Leu Ala Arg
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Gly His Leu Ser Arg
1               5

<210> SEQ ID NO 23
<211> LENGTH: 28
<212> TYPE: DNA
<213> ORGANISM: Homo sapiens

```
<400> SEQUENCE: 23
ggagtcaggt gcaccatggt gtctgttt                                      28

<210> SEQ ID NO 24
<211> LENGTH: 28
<212> TYPE: DNA
<213> ORGANISM: Homo sapiens

<400> SEQUENCE: 24
gtggagaagt ctgccgttac tgccctgt                                      28

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
gacaggtacg gctgtcatca                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cagcctaagg gtgggaaaat                                               20

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
atgcttagaa ccgaggtaga gttt                                          24

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cctgagactt ccacactgat g                                             21

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaagtctgcc gttactgcg                                                19
```

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cccagtttct attggtctcc                                              20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ctcggtgcct ttagtgatgg                                              20

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gactcaccct gaagttctc                                               19

<210> SEQ ID NO 33
<211> LENGTH: 44
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 33
acacgacgct cttccgatct nnnngggctg ggcataaaag tcag                   44

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gacgtgtgct cttccgatct tccacatgcc cagtttctat t                      41

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base

```
<222> LOCATION: (21)..(24)
<223> OTHER INFORMATION: a, c, t, g, unknown or other

<400> SEQUENCE: 35
acacgacgct cttccgatct nnnntaaaag gcagggcaga gtcga          45

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacgtgtgct cttccgatct acatgcccag tttccatttg c              41

<210> SEQ ID NO 37
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 37
acacgacgct cttccgatct nnnnctgctt ccgacacagc tgcaa          45

<210> SEQ ID NO 38
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gacgtgtgct cttccgatct tcacccttca ttcccatgca t              41

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (21)..(24)
<223> OTHER INFORMATION: a, c, t, g, unknown or other

<400> SEQUENCE: 39
acacgacgct cttccgatct nnnnggaacg tctgaggtta tcaat          45

<210> SEQ ID NO 40
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gacgtgtgct cttccgatct tccttccctc ccttgtcc                  38
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41 ggttcattttt tcattctcac a                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtaatctgag ggtaggaaaa c                                               21

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gagactgtgg gatagtcata                                                 20

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cattatcaca aacttagtgt cc                                              22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
agtctatgaa atgacaccat at                                              22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcaaaggcta taaaaaaaat tagc                                            24

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
gagatcatcc aggtgctttg                                              20

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ggcaaaggct ataaaaaaaa ttaagca                                      27

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gagatcatcc aggtgcttta                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
acatttgctt ctgacacaac                                              20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
gaaattggac agcaagaaag c                                            21

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cacccttgac caatagattc                                              20

```
<210> SEQ ID NO 53
<211> LENGTH: 18
<212> TYPE: DNA
<213> ORGANISM: Homo sapiens

<400> SEQUENCE: 53
gaggagaagt ctgccgtt                                                 18

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
gaagaaaaaa gcgctgtg                                                 18

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Lys Gln Asn Leu Asp Ala
1               5

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Asn Cys Ala Arg Leu Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Asn Gln Thr Arg Leu Asn
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

His His His Ser Leu Lys Arg
1               5
```

```
<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Asn Ser Glu Leu Asp Arg
1               5

<210> SEQ ID NO 60
<211> LENGTH: 18
<212> TYPE: DNA
<213> ORGANISM: Homo sapiens

<400> SEQUENCE: 60
gaggagaagt ctgccgtt                                                    18

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
gaggaaaagt ctgccgtt                                                    18

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
gaggagaaat ctgccgtt                                                    18

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gaggagaagt ctgctgtt                                                    18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
gaggaaaaat ctgccgtt                                                    18

<210> SEQ ID NO 65
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 65
gaggaaaagt ctgctgtt                                                 18

<210> SEQ ID NO 66
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
gaggagaaat ctgctgtt                                                 18

<210> SEQ ID NO 67
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gaggaaaaat ctgctgtt                                                 18

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
gaagaaaaat ctgccgtt                                                 18

<210> SEQ ID NO 69
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
gtggaaaaat ctgccgtt                                                 18

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gtagaaaaat ctgccgtt                                                 18

<210> SEQ ID NO 71
<211> LENGTH: 9
<212> TYPE: PRT
<213> ORGANISM: Unknown
```

```
<220> FEATURE:
<223> OTHER INFORMATION: Description of Unknown: 'LAGLIDADG' family
      meganuclease motif peptide

<400> SEQUENCE: 71

Leu Ala Gly Leu Ile Asp Ala Asp Gly
1               5
```